United States Patent
Elmaleh et al.

(10) Patent No.: US 8,450,466 B2
(45) Date of Patent: May 28, 2013

(54) COMPOUNDS AND COMPOSITIONS FOR THE DETECTION AND TREATMENT OF ALZHEIMER'S DISEASE AND RELATED DISORDERS

(75) Inventors: David R. Elmaleh, Newton, MA (US); Timothy M. Shoup, Waltham, MA (US); Hongning Fu, Newton, MA (US)

(73) Assignees: The General Hosptial Corporation, Charlestown, MA (US); Fluoropharma, Inc., Boston, MA (US)

( * ) Notice: Subject to any disclaimer, the term of this patent is extended or adjusted under 35 U.S.C. 154(b) by 195 days.

(21) Appl. No.: 12/933,139

(22) PCT Filed: Mar. 23, 2009

(86) PCT No.: PCT/US2009/037928
§ 371 (c)(1),
(2), (4) Date: Nov. 19, 2010

(87) PCT Pub. No.: WO2009/117728
PCT Pub. Date: Sep. 24, 2009

(65) Prior Publication Data
US 2011/0060138 A1 Mar. 10, 2011

Related U.S. Application Data

(60) Provisional application No. 61/038,571, filed on Mar. 21, 2008.

(51) Int. Cl.
*C07H 17/02* (2006.01)
*C07D 215/00* (2006.01)

(52) U.S. Cl.
USPC ............................ 536/17.6; 536/17.4; 546/16

(58) Field of Classification Search
USPC .................................. 536/17.4, 17.6; 546/16
See application file for complete search history.

(56) References Cited

U.S. PATENT DOCUMENTS

| | | | |
|---|---|---|---|
| 4,804,665 A | 2/1989 | Goto et al. | |
| 5,852,029 A | 12/1998 | Fisher et al. | |
| 2005/0119319 A1 | 6/2005 | Meese et al. | |
| 2006/0117397 A1 | 6/2006 | Rutkowski et al. | |
| 2007/0197452 A1 | 8/2007 | McLaurin | |

FOREIGN PATENT DOCUMENTS

| | | |
|---|---|---|
| CH | 375356 | 2/1964 |
| GB | 1 041 015 | 9/1966 |
| WO | WO-85/00171 | 1/1985 |
| WO | WO-2007/041855 | 4/2007 |
| WO | WO-2007/119108 | 10/2007 |

OTHER PUBLICATIONS

Cignarella et al., "Synthesis of a new series of 2,8-disubstituted-2,8-diazaspiro[4,5]decan-1-ones as potential muscarinic agonists," Eur. J. Med. Chem., 29:955-961 (1994).
Mailey et al., "Synthesis of Derivatives of Alkylated and Arylated Piperidones and Piperidinols," Journal of Organic Chemistry, 22:1061-1065 (1957).
Nagai et al., "Studies on Psychotropic Agents. I. Synthesis of 3,8-Disubstituted-1-oxa-3,8-diazaspiro[4,5]decan-2,4-dione Derivatives," Chem. Pharm. Bull., 24(6):1179-1188 (1976).
Süess, von Rudolf, "Regiospezifische Reduktionen von 1,3,3-trisubstituierten Succinimiden mit Diboran," Helvetica Chimica Acta, 60:(5):1650-1656 (1977).
Tsukamoto et al., "Synthesis and Structure-Activity Studies of a Series of Spirooxazolidine-2,4-diones: 4-Oxa Analogues of the Muscarinic Agonist 2-Ethyl-8-methyl-2,8-diazaspiro[4,5]decane-1,3-dione," J. Med. Chem., 36:2292-2299 (1993).
Valenta et al., "Potential Cholinergic and Anticholinergic Compounds: Synthesis of 2,8-Substituted 2,8-Disazaspiro[4,5]Decane-1,3-Diones," Collect. Czech. Chem. Commun., 55:2304-2316 (1990).
European Search Report dated Apr. 14, 2011 from 09723502.2.
International Search Report dated Dec. 14, 2009 from PCT/US2009/037928.

*Primary Examiner* — Elli Peselev
(74) *Attorney, Agent, or Firm* — Foley Hoag LLP

(57) ABSTRACT

One aspect of the present invention relates to compounds, compositions and methods for diagnosis and/or treatment of a subject suffering from an amyloidosis-associated pathological condition. In certain embodiments, the imaging and/or therapeutic agents of the instant invention may be administered to a subject for identification and/or treatment of amyloid deposits. A specific imaging method detects amyloid deposits by administering the imaging agent to the subject and detecting the spatial distribution of the agent. Differential accumulation of the agent is indicative of AD or an amyloidosis-associated pathological condition and can be monitored by using a PET or SPECT camera.

15 Claims, 10 Drawing Sheets

Figure 1

| Tissue | % dose per gram +/- SD; six rats per time point | | |
|---|---|---|---|
| | 5 min | 30 min | 60 min |
| Blood | 0.345+/-0.06 | 0.35+/-0.06 | 0.26+/-0.02 |
| Heart | 0.348+/-0.02 | 0.35+/-0.02 | 0.25+/-0.02 |
| Lung | 0.41+/-0.04 | 0.41+/-0.04 | 0.35+/-0.03 |
| Liver | 0.43+/-0.07 | 0.43+/-0.07 | 0.43+/-0.05 |
| Spleen | 0.74+/-0.17 | 0.74+/-0.17 | 0.48+/-0.16 |
| Kidney | 1.88+/-0.39 | 1.88+/-0.39 | 1.65+/-0.16 |
| Adrenal Gland | 0.45+/-0.08 | 0.45+/-0.08 | 0.31+/-0.03 |
| Stomach | 0.35+/-0.16 | 0.35+/-0.16 | 0.78+/-0.26 |
| GI Tract | 0.34+/-0.08 | 0.34+/-0.08 | 0.56+/-0.11 |
| Gonads | 0.10+/-0.02 | 0.10+/-0.02 | 0.41+/-0.02 |
| Skeletal Muscle | 0.26+/-0.08 | 0.26+/-0.08 | 0.24+/-0.02 |
| Bone | 0.31+/-0.03 | 0.31+/-0.09 | 0.33+/-0.02 |
| Brain | 0.27+/-0.06 | 0.27+/-0.06 | 0.45+/-0.02 |

Figure 2

| Tissue | % dose per gram +/- SD; six rats per time point | |
| :---: | :---: | :---: |
| | 30 min | 60 min |
| Blood | 0.33+/-0.08 | 0.26+/-0.05 |
| Heart | 0.25+/-0.02 | 0.17+/- 0.01 |
| Lung | 0.30+/-0.04 | 0.27+/-0.01 |
| Liver | 0.75+/-0.30 | 0.68+/-0.05 |
| Spleen | 0.55+/-0.05 | 0.34+/-0.02 |
| Kidney | 1.32+/-0.13 | 0.96+/-0.08 |
| Adrenal Gland | 0.31+/-0.14 | 0.27+/-0.03 |
| Stomach | 0.57+/-0.11 | 0.48+/-0.12 |
| GI Tract | 0.56+/-0.05 | 0.42+/-0.05 |
| Gonads | 0.31+/-0.02 | 0.26+/-0.09 |
| Skeletal Muscle | 0.32+/-0.25 | 0.17+/-0.02 |
| Bone | 0.87+/-0.31 | 1.67+/-0.49 |
| Brain | 0.34+/-0.02 | 0.20+/-0.02 |

1-deoxy-1-[18F]fluoro-scyllo-inositol

Figure 10

| Organ Affected | Possible Consequences |
| --- | --- |
| Brain | Alzheimer's disease |
| Heart | Heart failure, abnormal heart rhythms (arrhythmias), enlarged heart |
| Kidneys | Kidney failure; fluid accumulation in the tissues, causing swelling (edema) |
| Nervous system | Numbness, tingling, weakness |
| Digestive system | Intestinal obstruction, poor nutrient absorption, enlarged tongue |
| Blood and blood vessels | Easy bruising |
| Lungs | Difficulty breathing |
| Skin | Skin papules, bruises, enlarged lymph nodes |
| Thyroid gland | Enlarged thyroid gland |
| Liver | Enlarged liver |
| Musculoskeletal system | Carpal tunnel syndrome |
| Lymph nodes | Enlarged lymph nodes |

COMPOUNDS AND COMPOSITIONS FOR THE DETECTION AND TREATMENT OF ALZHEIMER'S DISEASE AND RELATED DISORDERS

RELATED APPLICATIONS

This application is the U.S. National Stage of International Patent Application No. PCT/US2009/037928, filed Mar. 23, 2009, which claims the benefit of priority to U.S. Provisional Patent Application Ser. No. 61/038,571 filed Mar. 21, 2008; each of which is hereby incorporated by reference in its entirety.

BACKGROUND

Millions of Americans suffer from dementia and other cognitive deficits as a result of Alzheimer's disease (AD), a neurodegenerative disease. Due to its occurrence in the brain, it is difficult to diagnose the condition and to determine its cause without dangerous brain biopsy. Scientists believe that as many as 4.5 million Americans suffer from AD. AD usually begins after age 60 and its risk goes up with age. The cause of AD is unknown and, at present, no cure has been found.

AD can only be definitely confirmed after an autopsy, which prevents early accurate diagnosis and treatment of the condition. Neuropathologically, AD is characterized by the presence of neuritic plaques, neurofibrillary tangles and neuronal loss. See *Mann. Mech. Ageing Dev.* 1985, 3(1), 213. Doctors can diagnose AD correctly up to 90 percent using several tools to diagnose "probable" AD, namely, (1) questions about the person's general health, past medical problems, and ability to carry out daily activities; (2) tests of memory, problem solving, attention, counting, and language; (3) medical tests, such as tests of blood, urine, or spinal fluid; and (4) brain scans.

Postmortem brain tissues of AD victims show the presence of amyloid cores of neuritic plaques that are composed of amyloid β-(Aβ-) protein being predominantly arranged in beta-pleated sheet configuration. See *J. Biol. Chem.* 1992, 267(24), 17082; and *Proc. Natl. Acad. Sci., USA* 1986, 83(2), 503.

Deposition of amyloid β-(Aβ-) protein occurs, however, not only in individuals that have AD, but it also frequent among individuals who are undergoing the aging process. Thus, it is very critical to distinguish the AP production due to the normal aging process or to AD or other dementia-causing diseases such as DLB dementia associated with Louis Body. In the normal aging process, non-compact or diffuse amyloid plaques containing less fibrillar AP are deposited primarily in the brain. In contrast, AD patients have brains that are characterized by an unanatomically widespread process of amyloid deposition and neurite plaque formation containing dense amyloid fibrils.

Clinical tests to determine the onset of AD and its progression are not presently sensitive and several agents are reported as potential PET and SPECT imaging tracers. Some of the developmental research on imaging agents useful for the diagnosis of AD and other related diseases are discussed below.

U.S. Patent Publication Application No. 2006/0018825 A1, assigned to BF Research Institute, hereby incorporated by reference, describes a series of BF compounds or a salt or solvate thereof that can be used as a probe for the imaging and diagnosis of diseases in which amyloid P-protein accumulates. These compounds have high specificity for diffuse plaques and act as early indicators of AD. In addition, they have rapid clearance from the brain.

Okamura et al. (in *J. Neurosci.* 2004, 24(10), 2535) describes a labeled sterylbenzoxazole derivative compound, $^{18}$F-radio labeled 6-(2-fluoroethoxy)-2-[2-(4-methylaminophenyl)ethenyl]-benzoxazole (BF-168), that demonstrated abundant initial brain uptake (3.9% injected dose/gm at 2 min after injection) and fast clearance ($t_{1/2}$=24.7 min) after intravenous (iv) administration in normal mice. In addition, autoradiograms of brain sections from APP23 transgenic mice at 180 min after iv injection of $^{18}$F-radiolabeled BF-168 showed selective labeling of brain amyloid deposits with little non-specific binding.

More recently, Kudo et al. (in *J. Nucl. Med.* 2007, 48553) have demonstrated the use of a novel compound, F-18 labeled 2-(2-[2-diethylaminothiazol-5-yl]-ethenyl)-6-(2-[fluoro]) ethoxybenzoxazol (eB F-227) as a promising PET probe for in vivo detection of dense amyloid deposits in AD patients.

U.S. Pat. Nos. 6,001,331 and 6,696,039 B2, issued Dec. 14, 1999 and Feb. 24, 2004, respectively, hereby incorporated by reference, describe the use of several radiolabeled benzothiazole compounds for imaging amyloid deposits.

U.S. Pat. Nos. 6,168,776 and 6,133,259, issued Jan. 2, 2001 and Oct. 17, 2000, respectively, hereby incorporated by describe amyloid-binding compounds such as Chrysamine G and their use in identifying AD in vivo and other pathological conditions characterized by amyloidosis.

One promising amyloid imaging agent is an analogue of thioflavin T, also known as the Pittsburgh Compound-B or "PIB compound." PIB is also known as [N-methyl-($^{11}$C)]-2-(4'-methylaminophenyl)-6-hydroxybenzothiazole (or [$^{11}$C] 6-OH-BTA-I). PET imaging with $^{11}$C-PIB can discriminate AD from frontotemporal lobar degeneration (FTLD). See *J. Med. Chem.* 2003, 46(13), 2740; and *Neurology* 2007, 68, 1205. However, use of a C-11 labeled tracer limits imaging to medical centers with a cyclotron.

It is well known that 2,8-diazaspiro[4,5]decane-1,3-dione (RS-86) derivatives are active and centrally effective muscarinic cholinergic agonists, with analgesic and sedative properties in animals when given orally. In addition, it has been shown that the C-11 radiolabeled version of 2,8-diazaspiro [4,5]decane-1,3-dione can be used as a tracer, though the reported study describes brain distribution results with a very low specific activity. Further, the biodistribution of the C-11 radiolabeled 2,8-diazaspiro[4,5]decane-1,3-dione in rats, as a function of time, showed that the initial brain uptake was about 1.1%, with high concentrations of percent dose per gram in areas rich with muscarinic receptors such as caudate, putamen and thalamus. However, as discussed above with respect to $^{11}$C-PIB, the utility of a C-11 labeled tracer is limited to medical centers with a cyclotron.

Accordingly, there is a need to provide compounds and methods for imaging and treating AD and amyloidosis-associated pathological conditions that are easily available and cost effective. There is a continuing need to seek novel imaging tracers that are accurate and used in early detection of AD and other related pathological conditions.

SUMMARY

One aspect of the present invention relates to compounds, compositions and methods for diagnosis and/or treatment of a subject suffering from an amyloidosis-associated pathological condition. In certain embodiments, the imaging and/or therapeutic agents of the instant invention may be administered to a subject for identification and/or treatment of amyloid deposits. A specific imaging method detects amyloid deposits by administering the imaging agent to the subject and detecting the spatial distribution of the agent. Differential accumulation of the agent is indicative of AD or an amyloidosis-associated pathological condition and can be monitored by using a PET or SPECT camera.

One aspect of the invention relates to the preparation of fluorinated or radiofluorinated 2,8-diazaspiro[4,5]decane-1, 3-diones, and their diagnostic and/or therapeutic use in brain disorders associated with aging, such as, senile dementia and Alzheimer's disease.

Another aspect of the invention relates to the preparation of fluorinated or radiofluorinated inositols (such as 1-deoxy-1-fluoro-scyllo-inositol and 1-deoxy-1-fluoro-myo-inositol), and their diagnostic and/or therapeutic use in brain disorders associated with aging, such as, senile dementia and Alzheimer's disease.

Another aspect of the invention relates to compounds which are a combination of an inositol and a 2,8-diazaspiro[4,5]decane-1,3-dione (e.g., wherein the inositol is covalently linked by a cross-linker to the 2,8-diazaspiro[4,5]decane-1,3-dione), and their diagnostic and/or therapeutic use in brain disorders associated with aging, such as, senile dementia and Alzheimer's disease.

Another aspect of the invention relates to optionally fluorinated or radiofluorinated combinations of 2,8-diazaspiro[4,5]decane-1,3-diones and D-glucose (e.g. [F-18]-2-fluoro-2-deoxy-D-glucose), and their diagnostic and/or therapeutic use in brain disorders associated with aging, such as, senile dementia and Alzheimer's disease. In certain embodiments, the 2,8-diazaspiro[4,5]decane-1,3-dione improves the selectivity and or uptake of the glucose.

Another aspect of the invention relates to the optionally fluorinated or radiofluorinated combination of an inositol with D-glucose (e.g. [F-18]-2-fluoro-2-deoxy-D-glucose), and their diagnostic and/or therapeutic use in brain disorders associated with aging, such as, senile dementia and Alzheimer's disease. In certain embodiments, the inositol improves the selectivity and/or uptake of the glucose.

Other aspects, features, objects, and advantages of the present invention are apparent in the detailed description that follows. It should be understood, however, that the detailed description is given by way of illustration only, not limitation. Various changes and modifications within the scope of the invention will become apparent to those skilled in the art from the detailed description.

BRIEF DESCRIPTION OF THE FIGURES

FIG. 1 depicts a table showing the biodistribution in rats following the injection of [F-18]-N-2-fluoroethyl-2,8-diazaspiro[4,5]decane-1,3-dione at three different time points.

FIG. 2 depicts a table showing the biodistribution in rats following the injection of [F-18]-N-2-fluoropropyl-2,8-diazaspiro[4,5]decane-1,3-dione at two different time points.

FIG. 10 depicts a table showing the some of the effects of amyloid buildup.

DETAILED DESCRIPTION

Figure 3:
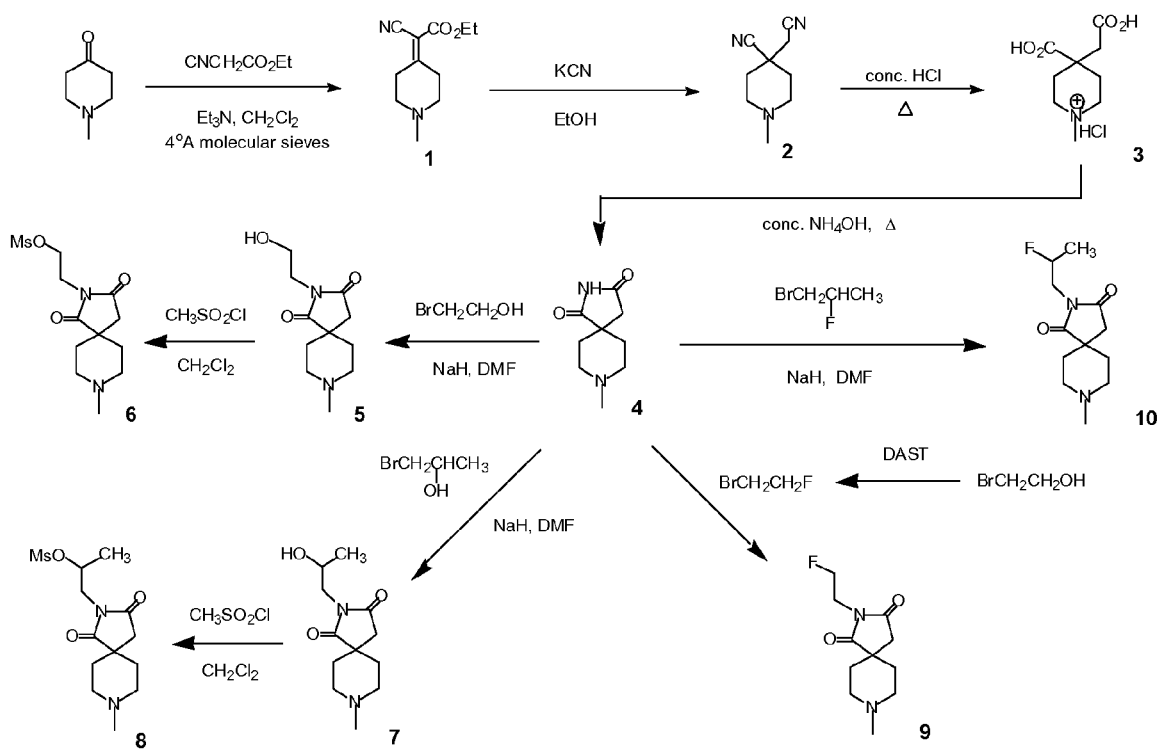
FIG. 3 depicts one approach to the synthesis of two fluorinated 2,8-diazaspiro[4,5]decane-1,3-dione derivatives.

One aspect of the present invention provides embodiments of compounds, compositions and methods for effective administration to a subject suffering from amylodiosis-associated pathological conditions, such as Alzheimer's disease (AD). In certain embodiments of the invention, the compounds are reversible choline esterase inhibitors that show high brain uptake. In certain embodiments, the compounds inhibit β-(Aβ-) protein folding that causes amyloid plaque formation. Further, in certain embodiments, the compounds are labeled with a PET or SPECT radionuclide, and can be used for diagnosing amyloid deposits in patients suffering from Alzheimer's disease and/or pathological conditions characterized by the presence of amyloid deposits. In certain embodiments, the novel imaging compounds act on both potential Alzheimer disease progressions.

One aspect of the invention relates to the preparation of fluorinated or radiofluorinated 2,8-diazaspiro[4,5]decane-1,3-diones, and their diagnostic and/or therapeutic use in amylodiosis-associated pathological conditions. For example in brain disorders associated with aging, such as, senile dementia and Alzheimer's disease. In certain embodiments, the compositions comprise an effective amount of a fluorinated 2,8-diazaspiro[4,5]decane-1,3-dione, in combination with a pharmaceutical carrier in an appropriate dosage. In certain embodiments, the compositions comprise a diagnostic radioimaging amount of a $^{18}$F-labeled fluorinated 2,8-diazaspiro[4,5]decane-1,3-dione, in combination with a pharmaceutical carrier in an appropriate dosage.

Another aspect of the invention relates to compounds which are a combination of a scyllo-inositol and a 2,8-diazaspiro[4,5]decane-1,3-dione (e.g., wherein a scyllo-inositol is covalently linked by a cross-linker to a 2,8-diazaspiro[4,5]decane-1,3-dione). Some of such compounds may be reversible acetyl choline esterase inhibitors and/or Aβ-amyloid plaque formation inhibitors; in addition, as such, some compounds may be useful for imaging and treating brain disorders associated with aging, such as, for example, senile dementia and Alzheimer's disease. In certain embodiments, certain compounds which are combinations of a scyllo-inositol and a 2,8-diazaspiro[4,5]decane-1,3-dione may show improved brain uptake and/or brain bioavailability compared to the scyllo-inositol and/or the 2,8-diazaspiro[4,5]decane-1,3-dione. Therefore, such compounds may improve the effective action of the compound comprising the combination over one or both of the individual compounds. In certain embodiments, certain compositions of the invention comprise a therapeutically and/or diagnostically effective amount of a composition comprising a compound which is a combination of scyllo-inositol and a radiofluorinated 2,8-diazaspiro[4,5]decane-1,3-dione, and a pharmaceutical carrier in an appropriate dosage.

Another aspect of the invention relates to combinations of 2,8-diazaspiro[4,5]decane-1,3-diones and D-glucose for therapy; and combinations with [F-18]-2-fluoro-2-deoxy-D-glucose for diagnosis. In certain embodiments, compositions of the invention comprise a therapeutically and/or diagnostically effective amount of a composition comprising a compound which is a combination of D-glucose or [F-18]-2-fluoro-2-deoxy-D-glucose and a 2,8-diazaspiro[4,5]decane-1,3-dione, and a pharmaceutical carrier in an appropriate dosage.

Another aspect of the invention relates to the combination of scyllo-inositol with D-glucose for improving uptake and therapy; and combinations with [F-18]-2-fluoro-2-deoxy-D-glucose for diagnosis. In certain embodiments, compositions of the invention comprise a therapeutically and/or diagnostically effective amount of a composition comprising a compound which is a combination of D-glucose or [F-18]-2-fluoro-2-deoxy-D-glucose and a scyllo-inositol, and a pharmaceutical carrier, in an appropriate dosage.

In certain embodiments, imaging and/or therapeutic agents of the instant invention may be administered to a subject for identification of amyloid deposits. A specific imaging method detects amyloid deposits by administering the imaging agent to the subject and detecting the spatial distribution of the agent. Differential accumulation of the agent is indicative of AD or an amyloidosis-associated pathological condition and can be monitored by using a PET or SPECT camera.

DEFINITIONS

Herein a number of terms are used extensively. The following definitions are provided to facilitate understanding of the invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" or, when used in the claims, "consisting of" will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of" or "exactly one of." "Consisting essentially of" when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of" and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Amyloidosis is a condition characterized by the accumulation of various insoluble, fibrillar proteins in the tissues of a patient. An amyloid deposit is formed by the aggregation of amyloid proteins, followed by the further combination of aggregates and/or amyloid proteins.

As used herein, "amylodiosis-associated pathological conditions" refers to a group of disorders caused by abnormal folding of proteins leading to fibril formation in one or more body organs, systems or soft tissues. These clumps of protein are called amyloid deposits and the accumulation of amyloid deposits causes the progressive malfunction and eventual failure of the affected organ. Normally, proteins are broken down at about the same rate as they are produced, but these unusually stable amyloid deposits are deposited more rapidly than they can be broken down. The accumulation may be localized in one organ or may be systemic such that several organs are affected.

Amyloidosis causes few or no symptoms in some people, while producing severe symptoms and fatal complications in other people. The severity of the disease depends on which organs are affected by amyloid deposits. Amyloidosis is twice as common in men as in women and is more common among older people.

Many forms of amyloidosis exist, and the disease can be classified into four groups: primary amyloidosis, secondary amyloidosis, hereditary amyloidosis, and amyloidosis associated with normal aging.

Primary amyloidosis (light chain amyloidosis) occurs with abnormalities of plasma cells, and some people with primary amyloidosis also have multiple myeloma (cancer of the plasma cells). Typical sites of amyloid buildup in primary amyloidosis are the heart, lungs, skin, tongue, thyroid gland, intestines, liver, kidneys, and blood vessels.

Secondary amyloidosis may develop in response to various diseases that cause persistent infection or inflammation, such as tuberculosis, rheumatoid arthritis, and familial Mediterranean fever. Typical sites of amyloid buildup in secondary amyloidosis are the spleen, liver, kidneys, adrenal glands, and lymph nodes.

Hereditary amyloidosis has been noted in some families, particularly those from Portugal, Sweden, and Japan. The amyloid-producing defect occurs because of mutations in specific proteins in the blood. Typical sites for amyloid buildup in hereditary amyloidosis are the nerves, heart, blood vessels, and kidneys.

Amyloidosis associated with normal aging usually affects the heart. What causes amyloid to build up in the heart, other than age, usually is not known. Amyloid also accumulates in the brain of people with Alzheimer's disease and is thought to play a role in causing Alzheimer's. See FIG. 10 for a table showing the effects of amyloid buildup.

Besides its presence in Alzheimer's disease, amyloid deposits has also been shown in diseases such as Mediterranean fever, Muckle-Wells syndrome, idiopathic myeloma, amyloid polyneuropathy, amyloid cardiomyopathy, systemic senile amyloidosis, amyloid polyneuropathy, hereditary cerebral hemorrhage with amyloidosis, Down's syndrome, Scrapie, Creutzfeldt-Jacob disease, Kum, Gerstamnn-Straussler-Scheinker syndrome, medullary carcinoma of the thyroid, Isolated atrial amyloid, $\beta_2$-microglobulin amyloid in dialysis patients, inclusion body myositis, $\beta_2$-amyloid deposits in muscle wasting disease, and Islets of Langerhans diabetes Type I1 insulinoma.

The term "heteroatom" is art-recognized and refers to an atom of any element other than carbon or hydrogen. Illustrative heteroatoms include boron, nitrogen, oxygen, phosphorus, sulfur and selenium.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 80 or fewer carbon atoms in its backbone (e.g., $C_1$-$C_{80}$ for straight chain, $C_3$-$C_{80}$ for branched chain), and alternatively, about 30 or fewer. Likewise, cycloalkyls have from about 3 to about 10 carbon atoms in their ring structure, and alternatively about 5, 6 or 7 carbons in the ring structure. As used herein, "fluoroalkyl" denotes an alkyl where one or more hydrogens have been replaced with fluorines; "perfluoroalkyl" denotes an alkyl where all the hydrogens have been replaced with fluorines.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "alkylene," is art-recognized, and as used herein, pertains to a bidentate moiety obtained by removing two hydrogen atoms, either both from the same carbon atom, or one from each of two different carbon atoms, of a hydrocarbon compound, which may be aliphatic or alicyclic, or a combination thereof, and which may be saturated, partially unsaturated, or fully unsaturated. Examples of linear saturated $C_{1-10}$alkylene groups include, but are not limited to, —$(CH_2)_n$— where n is an integer from 1 to 10, for example, —$CH_2$—(methylene), —$CH_2CH_2$— (ethylene), —$CH_2CH_2CH_2$— (propylene), —$CH_2CH_2CH_2CH_2$— (butylene), —$CH_2CH_2CH_2CH_2CH_2$— (pentylene) and —$CH_2CH_2CH_2CH_2CH_2CH_2$— (hexylene). Examples of branched saturated $C_{1-10}$alkylene groups include, but are not limited to, —$CH(CH_3)$—, —$CH(CH_3)CH_2$—, —$CH(CH_3)CH_2CH_2$—, —$CH(CH_3)CH_2CH_2CH_2$—, —$CH_2CH(CH_3)CH_2$—, —$CH_2CH(CH_3)CH_2CH_2$—, —$CH(CH_2CH_3)$—, —$CH(CH_2CH_3)CH_2$—, and —$CH_2CH(CH_2CH_3)CH_2$—. Examples of linear partially unsaturated $C_{1-10}$alkylene groups include, but are not limited to, —CH═CH— (vinylene), —CH═CH—$CH_2$—, —CH═CH—$CH_2$—$CH_2$—, —CH═CH—$CH_2$—$CH_2$—$CH_2$—, —CH═CH—CH═CH—, —CH═CH—CH═CH—$CH_2$—, —CH═CH—CH═CH—$CH_2$—$CH_2$—, —CH═CH—$CH_2$—CH═CH—, and —CH═CH—$CH_2$—$CH_2$—CH═CH—. Examples of branched partially unsaturated $C_{1-10}$alkylene groups include, but are not limited to, —$C(CH_3)$═CH—, —$C(CH_3)$═CH—$CH_2$—, and —CH═CH—CH($CH_3$)—. Examples of alicyclic saturated $C_{1-10}$alkylene groups include, but are not limited to, cyclopentylene (e.g., cyclopent-1,3-ylene), and cyclohexylene (e.g., cyclohex-1,4-ylene). Examples of alicyclic partially unsaturated $C_{1-10}$alkylene groups include, but are not limited to, cyclopentenylene (e.g., 4-cyclopenten-1,3-ylene), and cyclohexenylene (e.g., 2-cyclohexen-1,4-ylene, 3-cyclohexen-1,2-ylene, and 2,5-cyclohexadien-1,4-ylene).

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, alkylthio, sulfonyl, sulfonamido, ketone, aldehyde, ester, heterocyclyl, aromatic or heteroaromatic moieties, trifluoromethyl, cyano, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, alkylthio, sulfonyl, ketone, aldehyde, ester, a heterocyclyl, an aromatic or heteroaromatic moiety, trifluoromethyl, cyano, or the like.

The term "nitro" is art-recognized and refers to —$NO_2$; the term "halo" or "halogen" is art-recognized and refers to —F, —Cl, —Br or —I, and as used herein also refers to radioactive forms thereof, such as $^{18}F$, $^{76}Br$, $^{77}Br$, $^{123}I$, $^{124}I$ and $^{125}I$; the term "sulfhydryl" is art-recognized and refers to —SH; the term "hydroxyl" means —OH; and the term "sulfonyl" is art-recognized and refers to —$SO_2^-$.

The terms "amine" and "amino" are art-recognized and refer to both unsubstituted and substituted amines, e.g., a moiety that may be represented by the general formulas:

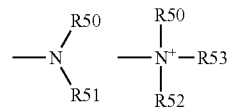

wherein R50, R51, R52 and R53 each independently represent a hydrogen, an alkyl, an alkenyl, —(CH$_2$)$_m$—R61, or R50 and R51 or R52, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

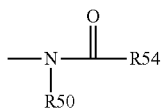

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

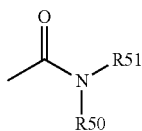

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carboxyl" is art recognized and includes such moieties as may be represented by the general formulas:

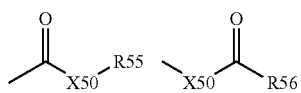

wherein X50 is a bond or represents an oxygen or a sulfur, and R55 and R56 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The term "carbamoyl" refers to —O(C=O)NRR', where R and R' are independently H, aliphatic groups, aryl groups or heteroaryl groups.

The term "oxo" refers to a carbonyl oxygen (=O).

The terms "oxime" and "oxime ether" are art-recognized and refer to moieties that may be represented by the general formula:

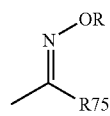

wherein R75 is hydrogen, alkyl, cycloalkyl, alkenyl, alkynyl, aryl, aralkyl, or —(CH$_2$)$_m$—R61. The moiety is an "oxime" when R is H; and it is an "oxime ether" when R is alkyl, cycloalkyl, alkenyl, alkynyl, aryl, aralkyl, or —(CH$_2$)$_m$—R61.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "sulfonate" is art recognized and refers to a moiety that may be represented by the general formula:

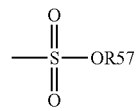

in which R57 is an electron pair, hydrogen, alkyl, cycloalkyl, or aryl.

The term "sulfate" is art recognized and includes a moiety that may be represented by the general formula:

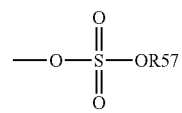

in which R57 is as defined above.

The term "sulfonamido" is art recognized and includes a moiety that may be represented by the general formula:

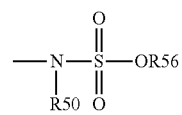

in which R50 and R56 are as defined above.

The term "sulfamoyl" is art-recognized and refers to a moiety that may be represented by the general formula:

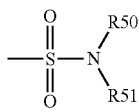

in which R50 and R51 are as defined above.

The term "sulfonyl" is art-recognized and refers to a moiety that may be represented by the general formula:

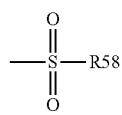

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

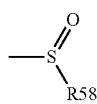

in which R58 is defined above.

The term "phosphoryl" is art-recognized and may in general be represented by the formula:

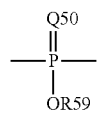

wherein Q50 represents S or O, and R59 represents hydrogen, a lower alkyl or an aryl. When used to substitute, e.g., an alkyl, the phosphoryl group of the phosphorylalkyl may be represented by the general formulas:

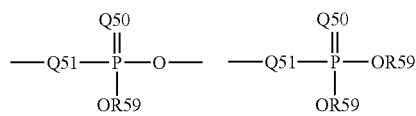

wherein Q50 and R59, each independently, are defined above, and Q51 represents O, S or N. When Q50 is S, the phosphoryl moiety is a "phosphorothioate".

The term "phosphoramidite" is art-recognized and may be represented in the general formulas:

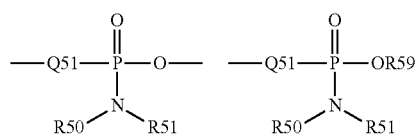

wherein Q51, R50, R51 and R59 are as defined above.

The term "phosphonamidite" is art-recognized and may be represented in the general formulas:

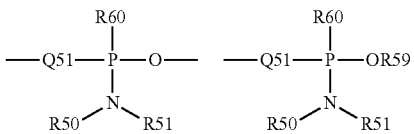

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The definition of each expression, e.g., alkyl, m, n, and the like, when it occurs more than once in any structure, is intended to be independent of its definition elsewhere in the same structure.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, "Handbook of Chemistry and Physics", 67th Ed., 1986-87, inside cover.

As used herein, the term "subject" or "individual" refers to a human or other vertebrate animal. It is intended that the term encompass "patients."

Figure 5:
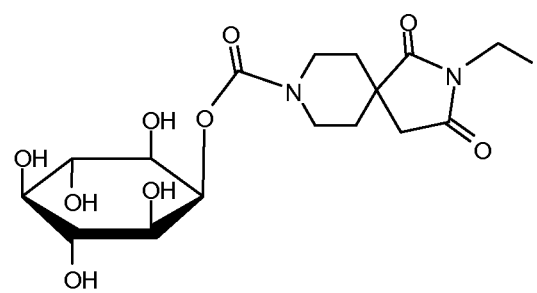
FIG. 5 depicts three examples of combinations of 2,8-diazaspiro[4,5]decane-1,3-dione and inositol structures.
Figure 5:
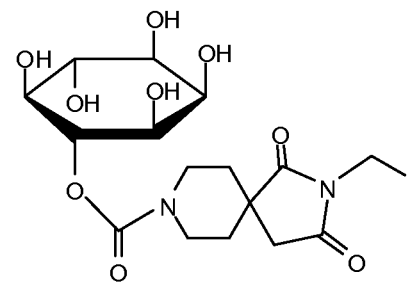
Figure 5:
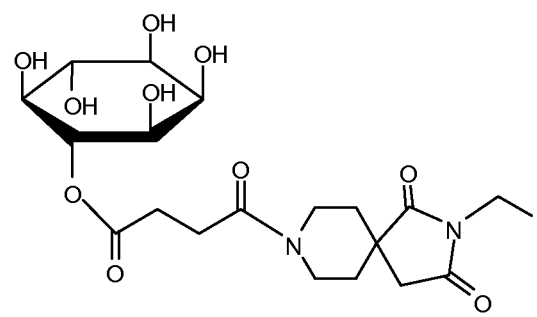

As used herein, a "combination" of two compounds indicates one compound wherein the two compounds have been linked by a cross linker For example, examples of combinations between 2,8-diazaspiro[4,5]decane-1,3-diones and inositol are shown in FIG. 5.

The term "diagnosis" as used herein refers to methods by which the skilled artisan can estimate and/or determine whether or not a patient is suffering from a given disease or condition. The skilled artisan often makes a diagnosis on the basis of one or more diagnostic indicators, i.e., a marker, the presence, absence, amount, or change in amount of which is indicative of the presence, severity, or absence of the condition.

The kit may also include at least one chelating structure and/or an auxillary molecule such as mannitol, gluconate, glucoheptonate and tartrate and a tin containing reducing agent.

The term "conjugated" refers to ionically or covalently attached (e.g., via a crosslinking agent).

A "chelating structure" refers to any molecule or complex of molecules that bind to a metal as well as the structure bound to a metal. In some embodiments, the metal can be radioactive (such as $^{99m}Tc$, $^{68}Cu$, $^{64}Cu$ and $^{68}Ga$). Examples of chelating structures include $N_2S_2$ structure, a HYNIC (hydrazinonicotinic acid) group-containing structure, a 2-methylthiolnicotinic acid groupcontaining structure, a carboxylate group-containing structure and the like. Additional discussion of chelating structures is below.

A "radioimaging agent" refers to a composition capable of generating a detectable image upon binding with a target and shall include radionuclides such as $^{18}F$, $^{76}Br$, $^{77}Br$, $^{123}I$, $^{124}I$, $^{125}I$, $^{99m}Tc$, $^{68}Cu$, $^{64}Cu$ and $^{68}Ga$.

A "fluorescence imaging agent" refers to a composition capable of generating a detectable optical imaging upon binding with a target with or without specific wave length of light activation and shall include fluorophores. The preferred fluorescence agents are near infra red light absorbing agents.

A "target" refers to an in vivo site to which imaging compounds binds. A preferred target is a brain tissue from a subject suffering from AD or an amyloidosis-associated pathological condition.

A "targeting molecule" is any molecule or biological entity that specifically accumulates in brain tissue from a subject suffering from AD or an amyloidosis-associated pathological condition.

Radioimaging methods that may be employed in accordance with the present inventions are known in the art. See U.S. Pat. No. 6,187,286 and U.S. Patent Publication No. 2006/0140859; both of which are hereby incorporated by reference.

In accordance with the invention, the targeting molecule is in association with (spatial proximity to) the radionuclide. Spatial proximity between the targeting molecule and the radionuclide may be effected in any manner which preserves the specificity of the targeting molecule for its target tissue. For example, spatial proximity between the radionuclide and the targeting molecule may be effected by a covalent or noncovalent chemical bond. Such a chemical bond may be effected through a chelating substance and/or an auxiliary molecule such as mannitol, gluconate, glucoheptonate, tartrate, and the like.

Alternatively, spatial proximity between the nuclide and the targeting molecule may be effected by incorporating the radionuclide and the targeting molecule in a micelle or liposome, in such a way that the affinity of the targeting molecule for its target tissue is maintained. Spatial proximity between the radionuclide and the targeting molecule may also be effected by attaching the radionuclide and the targeting molecule to a matrix such, as a microsphere or liposomes.

A radionuclide may be incorporated into the imaging agent by covalent bonding directly to an atom of the targeting molecule, or the radionuclide may be noncovalently or covalently associated with the targeting molecule through a chelating structure or through an auxiliary molecule such as mannitol, gluconate, glucoheptonate, tartrate, and the like. When a chelating structure is used to provide spatial proximity between the radionuclide and the targeting molecule, the chelating structure may be directly associated with the targeting molecule or it may be associated with the targeting molecule through an auxiliary molecule such as mannitol, gluconate, glucoheptonate, tartrate, and the like.

Any suitable chelating structure may be used to provide spatial proximity between the radionuclide and the targeting molecule of the agent through covalent or noncovalent association. Many such chelating structures are known in the art. Preferably, the chelating structure is an $N_2S_2$ structure, an $NS_3$ structure, an $N_4$ structure, an isonitrile containing structure, a hydrazine containing structure, a HYNIC (hydrazinonicotinic acid) group-containing structure, a 2-methylthiolnicotinic acid group-containing structure, a carboxylate group containing structure, and the like. In some cases, chelation can be achieved without including a separate chelating structure, because the radionuclide chelates directly to atom(s) in the targeting moiety, for example to oxygen atoms in the phosphate group(s) or in carboxylate group(s).

The chelating structure, auxiliary molecule, or radionuclide may be placed in spatial proximity to any position of the targeting molecule which does not interfere with the interaction of the targeting molecule with its receptor in tumors. The chelating structure, auxiliary molecule, or radionuclide may be covalently or non-covalently associated with any moiety of the targeting molecule except the receptor-binding moiety. For example, the chelating structure, auxiliary molecule, or radionuclide may be associated with the phosphate moiety of the targeting molecule, with the —X— moiety of the targeting molecule.

After the labeling reaction is complete, the reaction mixture may optionally be purified using one or more high performance liquid chromatography (HPLC) steps. Any suitable HPLC system may be used if a purification step is performed, and the yield of imaging agent obtained from the HPLC step may be optimized by varying the parameters of the HPLC system, as is known in the art. Any HPLC parameter may be varied to optimize the yield of the imaging agent of the invention. For example, the pH may be varied, e.g., raised, to decrease the elution time of the peak corresponding to the imaging agent of the invention.

The invention as embodied in a kit for radioimaging comprises a radioimaging agent described above, in combination with a pharmaceutically acceptable carrier such as human serum albumin. Human serum albumin for use in the kit of the invention may be made in any way, for example, through purification of the protein from human serum or though recombinant expression of a vector containing a gene encoding human serum albumin. Other substances may also be used as carriers in accordance with this embodiment of the invention, for example, detergents, dilute alcohols, carbohydrates, auxiliary molecules, and the like. The kit of the invention may of course also contain such other items as may facilitate its use, such as syringes, instructions, reaction vials, and the like.

In one embodiment, a kit according to the invention contains from about 1 to about 30 mCi of the radionuclide-labeled amyloid imaging agent described herein, in combination with a pharmaceutically-acceptable carrier. The amyloid imaging agent and carrier may be provided in solution or in lyophilized form. When the amyloid imaging agent and carrier of the kit are in lyophilized form, the kit may optionally contain a sterile and physiologically acceptable reconstitution medium such as water, saline, buffered saline, and the like.

The radioimaging agents of the invention may be used in accordance with the methods of the invention by those of skill in the art, e.g., by specialists in nuclear medicine, to image tissue in a mammal. Any mammalian tumor may be imaged the imaging agents of the invention. Images are generated by virtue of differences in the spatial distribution of the imaging agents which accumulate in the various tissues and organs of the mammal. The spatial distribution of the imaging agent accumulated in a mammal, in an organ, or in a tissue may be measured using any suitable means, for example, a PET or single photon emission computer tomography (SPECT) imaging camera apparatus, and the like.

PET imaging is accomplished with the aid of tracer compounds labeled with a positron-emitting isotope (Goodman, M. M. Clinical Positron Emission Tomography, Mosby Yearbook, 1992, K. F. Hubner et al., Chapter 14). These tracer compounds can be labeled with a positron-emitting radionuclide that includes $^{18}$F and $^{76}$Br. In general, a PET label, is a label which is covalently attached to the remainder of a molecule and should have a half life of at least about 5-20 minutes, preferably about 60 minutes or more. Examples of PET labels include $^{18}$F, $^{13}$N, $^{76}$Br (half life=16.1 hrs), $^{77}$Br, $^{15}$O, $^{68}$Ga (half life=68.3 min), $^{62}$Cu (half life=9.74 min), $^{64}$Cu (half life=12.7 hrs), $^{82}$Rb (half life=78 sec), and $^{24}$I (half life=4.18 days)

The use of $^{18}$F-labeled compounds in PET has thus far been limited to a few analog compounds. Most notably, 18-fluorodeoxyglucose has been widely used in studies of glucose metabolism and localization of glucose uptake associated with brain activity. More recently, other analogs, such as $^{18}$F-methyl choline (for prostate cancers; see *Cancer Res.* 2001, 6, 110), $^{18}$F-fluorothymidine (for lung tumors; see *J. Nucl. Med.* 2003, 44, 1426; and *Eur. J. Nuc. Mol. Imaging* 2003, 30, 1407) and O-(2-[$^{18}$F]fluoroethyl)-L-tyrosine (U.S. Pat. No. 7,138,540; hereby incorporated by reference), have also been employed in PET imaging. For examples of $^{18}$F-labeling imaging agents see: *Eur. J. Med. Chem.* 1994, 29, 115; *Eur. J. Med. Chem.* 1994, 29, 955; *J. Heterocyclic Chem.* 1993, 30, 1337; *Organic Process Research & Development* 2005, 9(6), 774; *J. Med. Chem.* 2005, 48(16), 5290; *J. Med. Chem.* 1990, 33, 1482; *Nuclear Medicine and Biology* 2001, 28(6), 683; and *Nuclear Medicine and Biology* 2004, 31(4), 483.

For SPECT imaging, the inventive compound can be labeled with a γ-emitting nuclide, such as, $^{99m}$Tc, $^{111}$In, $^{67}$Ga, $^{201}$Tl, $^{123}$Xe and others.

For fluorescence tomography imaging, the inventive compound can be conjugated to a near infra red moiety, such as CY5 (Cyanine dye). Fluorescence tomography is under development.

The imaging agents of the instant invention are used in the following manner. An effective amount of an imaging agent comprising at least one targeting molecule and a nuclide (from 1 to 50 mCi) may be combined with a pharmaceutically-acceptable carrier for use in imaging studies. In accordance with the invention, "an effective amount" of the imaging agent of the invention is defined as an amount sufficient to yield an acceptable image using equipment which is available for clinical use. An effective amount of the imaging agent of the invention may be administered in more than one injection. Effective amounts of the imaging agent of the invention will vary according to factors such as the degree of susceptibility of the individual, the age, sex, and weight of the individual, idiosyncratic responses of the individual, and the dosimetry. Effective amounts of the imaging agent of the invention will also vary according to instrument and film-related factors. Optimization of such factors is well within the level of skill in the art.

As used herein, "pharmaceutically-acceptable carrier" includes any and all solvents, dispersion media, coatings, antibacterial and antifungal agents, isotonic agents, absorption delaying agents, and the like. Pharmaceutically-acceptable carriers are materials, useful for the purpose of administering the compounds in the method of the present invention, which are preferably non-toxic, and may be solid, liquid, or gaseous materials, which are otherwise inert and pharmaceutically acceptable, and are compatible with the compounds of the present invention. Examples of such carriers include oils such as corn oil, buffers such as PBS, saline, polyethylene glycol, glycerin, polypropylene glycol, dimethylsulfoxide, an amide such as dimethylacetamide, a protein such as albumin, and a detergent such as Tween 80, mono- and oligopolysaccharides such as glucose, lactose, cyclodextrins and starch.

The formulation used in the present invention may also contain stabilizers, preservatives, buffers, antioxidants, or other additives known to those of skill in the art. The use of such media and agents for pharmaceutically-active substances is well known in the art. Supplementary active compounds can also be incorporated into the imaging agent of the invention. The imaging agent of the invention may further be administered to an individual in an appropriate diluent or adjuvant, co-administered with enzyme inhibitors or in an appropriate carrier such as human serum albumin or liposomes. Pharmaceutically-acceptable diluents include sterile saline and other aqueous buffer solutions. Adjuvants contemplated herein include resorcinols, non-ionic surfactants such as polyoxyethylene oleyl ether and n-hexadecyl polyethylene ether. Enzyme inhibitors include pancreatic trypsin inhibitor, diethylpyrocarbonate, and trasylol. Liposomes inhibitors include water-in-oil-in-water CGF emulsions, as well as conventional liposomes (see *J. Neuroimmunol.* 1984, 7, 27).

As described herein, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. See *J. Pharm. Sci.* 1977, 66, 1-19.

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, *J. Pham. Sci.* 1977, supra)

Preferably, the imaging agent of the present invention is administered intravenously, and the imaging agent will be formulated as a sterile, pyrogen-free, parenterally-acceptable aqueous solution. The preparation of such parenterally-acceptable solutions, having due regard to pH, isotonicity, stability, and the like, is within the skill in the art. A preferred formulation for intravenous injection should contain, in addition to the imaging agent, an isotonic vehicle such as Sodium Chloride Injection, Ringer's Injection, Dextrose Injection, Dextrose and Sodium Chloride Injection, Lactated Ringer's Injection, or other vehicle as known in the art.

The amount of imaging agent used for diagnostic purposes and the duration of the imaging study will depend upon the nature and severity of the condition being treated, on the nature of therapeutic treatments which the patient has undergone, and on the idiosyncratic responses of the patient. Ultimately, the attending physician will decide the amount of imaging agent to administer to each individual patient and the duration of the imaging study.

The diagnostic imaging amounts are preferably about 3 to 15 millicuries (mCi) for a 70 kg normal adult, more preferably being about 1-25 mCi for a 70 kg normal adult.

The ultimate solution form is preferably sterile. Sterilization can be accomplished by any art recognized technique, including but not limited to, addition of antibacterial of antifungal agents, for example, paraben, chlorobutanol, phenol, sorbic acid, thimerosal, and the like.

More specifically, the compounds that can be formulated into a pharmaceutical composition include a therapeutically-effective amount of the compound and a pharmaceutically-acceptable carrier. The therapeutically-effective amount of the compound and the specific pharmaceutically-acceptable carrier will vary depending upon, e.g., the age, weight, sex of the subject, the mode of administration, and the type of viral condition being treated.

In a particular aspect, the pharmaceutical composition which can be used includes the compounds of the present invention in effective unit dosage form. As used herein, the term "effective unit dosage" or "effective unit dose" is used herein to mean a predetermined amount sufficient to be effective against AD or the like.

The pharmaceutical compositions may contain the compound used in the method of this invention in an amount of from 0.01 to 99% by weight of the total composition, preferably 0.1 to 80% by weight of the total composition. For oral administration, the compound is generally administered in an amount of 0.1 g/body to 15 g/body, preferably 0.5 g/body to 5 g/body. For intravenous injection, the dose may be about 0.1 to about 30 mg/kg/day, preferably about 0.5 to about 10 mg/kg/day. If applied topically as a liquid, ointment, or cream, the compound may be present in an amount of about 0.1 to about 50 mg/mL, preferably about 0.5 to 30 mg/mL of the composition. Fluorescence agents will be administered in several µg/kg to several mg/kg. For example, 1-10 mg/kg.

When the compounds according to the invention are formulated for injection, the dose may be presented in unit dose form in ampoules or in multi-dose containers with added pharmaceutically-acceptable adjuvants such as a preservative.

In addition, the compositions may take forms such as suspensions, solutions, or emulsions in oily or aqueous vehicles, and may contain formulating agents, such as suspending, stabilizing, or dispersing agents, isotonic agents and/or dissolving co-solvents conventionally cited in the pharmaceutical art.

For systemic administration, the daily dosage as employed for adult human treatment will range from about 0.1 mg/kg to about 150 mg/kg, preferably about 0.2 mg/kg to about 80 mg/kg.

One aspect of the invention relates to a compound, or a pharmaceutically acceptable salt thereof, represented by formula I:

$$L-N\underset{[C(R^1)_2]_n}{\overset{[C(R^1)_2]_m}{\diagdown}}\underset{X}{\overset{Y}{\diagdown}}\underset{R^2}{\overset{X}{\diagup}}\quad I$$

wherein, independently for each occurrence,

X is —O— or —S—;

Y is —O—, —S—, —C($R^1$)$_2$—, —N($R^5$)— or —N[(C=O)$R^1$]—;

L is —$R^3$, —C(=O)$R^3$, —C(=O)[C($R^1$)$_2$]$_p$$R^3$, —C(=O)[C($R^1$)$_2$]$_p$C(=O)$R^3$, —[C($R^1$)$_2$]$_p$C(=O)$R^3$, —[C($R^1$)$_2$]$_p$$R^3$, —[C$_{1-10}$alkylene]$R^3$, —C(=O)[C$_{1-10}$alkylene]$R^3$, —[C$_{1-10}$alkylene]C(=O)$R^3$, —C(=O)[C$_{1-10}$alkylene]C(=O)$R^3$, an unsubstituted alkyl, or alkyl substituted with one or more substituents selected from the group consisting of halo, azido, hydroxy, alkoxy, aryloxy, heteroaryloxy, amino, alkylamino, arylamino, acylamino, heteroarylamino, nitro, sulfhydryl, imino, amido, phosphonate, phosphinate, oxycarbonyl, acyloxy, silyl, thioether, sulfo, sulfonate, sulfonyl, sulfonamido, formyl, cyano, isocyano, —(C($R^1$)$_2$)$_q$C($R^1$)$_3$ or a chelating structure;

R¹ is hydrogen, halo, azido, alkyl, haloalkyl, perhaloalkyl, fluoroalkyl, perfluoroalkyl, aralkyl, alkenyl, alkynyl, cycloalkyl, heterocyclyl, aryl, heteroaryl, aralkyl, heteroaralkyl, hydroxy, alkoxy, aryloxy, heteroaryloxy, aralkyloxy, heteroaralkyloxy, amino, alkylamino, arylamino, acylamino, heteroarylamino, nitro, sulfhydryl, imino, amido, phosphonate, phosphinate, acyl, carboxyl, oxycarbonyl, acyloxy, silyl, thioether, sulfo, sulfonate, sulfonyl, sulfonamido, formyl, cyano, isocyano or a chelating structure;

R² is —R³, —C(=O)R³, —C(=O)[C(R¹)₂]ₚR³, —C(=O)[C(R¹)₂]ₚC(=O)R³, —[C(R¹)₂]ₚC(=O)R³, —[C(R¹)₂]ₚR³, —[C₁₋₁₀alkylene]R³, —C(=O)[C₁₋₁₀alkylene]R³, —[C₁₋₁₀alkylene]C(=O)R³, —C(=O)[C₁₋₁₀alkylene]C(=O)R³, an unsubstituted alkyl, or alkyl substituted with one or more substituents selected from the group consisting of halo, azido, hydroxy, alkoxy, aryloxy, heteroaryloxy, amino, alkylamino, arylamino, acylamino, heteroarylamino, nitro, sulfhydryl, imino, amido, phosphonate, phosphinate, oxycarbonyl, acyloxy, silyl, thioether, sulfo, sulfonate, sulfonyl, sulfonamido, formyl, cyano, isocyano, —(C(R¹)₂)_qC(R¹)₃ or a chelating structure;

R³ is hydrogen, alkyl, heteroalkyl, cycloalkyl, heterocycloalkyl, aryl, heteroaryl, aralkyl, heteroaralkyl,

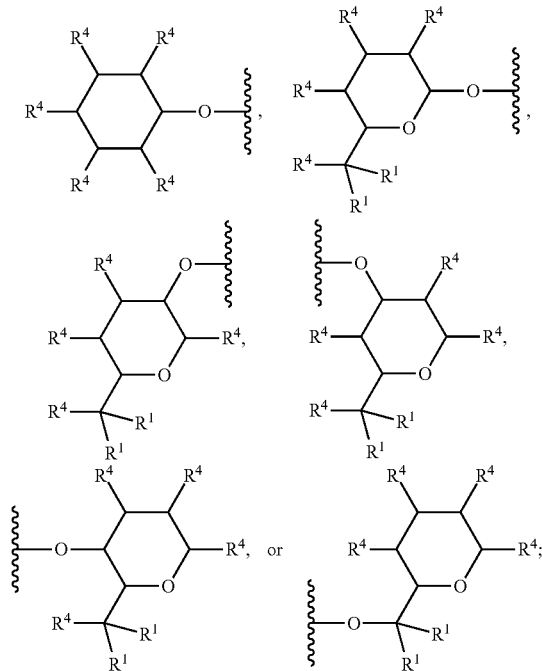

R⁴ is hydrogen, halo, azido, alkyl, haloalkyl, perhaloalkyl, fluoroalkyl, perfluoroalkyl, aralkyl, alkenyl, alkynyl, cycloalkyl, heterocyclyl, aryl, heteroaryl, aralkyl, heteroaralkyl, hydroxy, alkoxy, aryloxy, heteroaryloxy, aralkyloxy, heteroaralkyloxy, amino, alkylamino, arylamino, acylamino, heteroarylamino, nitro, sulfhydryl, imino, amido, phosphonate, phosphinate, acyl, carboxyl, oxycarbonyl, acyloxy, silyl, thioether, sulfo, sulfonate, sulfonyl, sulfonamido, formyl, cyano, isocyano, —OR⁵, —SR⁵, —N(R⁵)₂, —(C(R¹)₂)_qC(R¹)₃ or a chelating structure;

R⁵ is hydrogen, alkyl, heteroalkyl, cycloalkyl, heterocycloalkyl, aryl, heteroaryl, aralkyl, heteroaralkyl, acyl, —(C(R¹)₂)_qC(R¹)₃ or a chelating structure;

m is 1, 2 or 3;

n is 1, 2 or 3;

m plus n is 3 or 4 p is 1-10 inclusive; and q is 0-10 inclusive;

provided that when R² is an unsubstituted alkyl, or alkyl substituted with one or more substituents selected from the group consisting of halo, azido, hydroxy, alkoxy, aryloxy, heteroaryloxy, amino, alkylamino, arylamino, acylamino, heteroarylamino, nitro, sulfhydryl, imino, amido, phosphonate, phosphinate, oxycarbonyl, acyloxy, silyl, thioether, sulfo, sulfonate, sulfonyl, sulfonamido, formyl, cyano, isocyano, —(C(R¹)₂)_qC(R¹)₃ or a chelating structure, then L is —R³, —C(=O)R³, —C(=O)[C(R¹)₂]ₚR³, —C(=O)[C(R¹)₂]ₚC(=O)R³, —[C(R¹)₂]ₚC(=O)R³, —[C(R¹)₂]ₚR³, —[C₁₋₁₀alkylene]R³, —C(=O)[C₁₋₁₀alkylene]R³, —[C₁₋₁₀alkylene]C(=O)R³, —C(=O)[C₁₋₁₀alkylene]C(=O)R³;

and when L is an unsubstituted alkyl, or alkyl substituted with one or more substituents selected from the group consisting of halo, azido, hydroxy, alkoxy, aryloxy, heteroaryloxy, amino, alkylamino, arylamino, acylamino, heteroarylamino, nitro, sulfhydryl, imino, amido, phosphonate, phosphinate, oxycarbonyl, acyloxy, silyl, thioether, sulfo, sulfonate, sulfonyl, sulfonamido, formyl, cyano, isocyano, —(C(R¹)₂)_qC(R¹)₃ or a chelating structure, then R² is —R³, —C(=O)R³, —C(=O)[C(R¹)₂]ₚR³, —C(=O)[C(R¹)₂]ₚC(=O)R³, —[C(R¹)₂]ₚC(=O)R³, —[C(R¹)₂]ₚR³, —[C₁₋₁₀alkylene]R³, —C(=O)[C₁₋₁₀alkylene]R³, —[C₁₋₁₀alkylene]C(=O)R³, —C(=O)[C₁₋₁₀alkylene]C(=O)R³.

In certain embodiments, the present invention relates to any one of the aforementioned compounds and attendant definitions, wherein said compound comprises at least one ¹⁸F, ⁷⁶Br, ⁷⁷Br, ¹²³I, ¹²⁴I or ¹²⁵I.

In certain embodiments, the present invention relates to any one of the aforementioned compounds and attendant definitions, wherein said compound comprises at least one ¹⁸F.

In certain embodiments, the present invention relates to any one of the aforementioned compounds and attendant definitions, wherein said compound comprises only one chelating structure.

In certain embodiments, the present invention relates to any one of the aforementioned compounds and attendant definitions, wherein said compound comprises only one chelating structure; and ⁹⁹ᵐTc, ⁶⁸Cu, ⁶⁴Cu or ⁶⁸Ga chelated to the chelating structure.

In certain embodiments, the present invention relates to any one of the aforementioned compounds and attendant definitions, wherein X is —O—.

In certain embodiments, the present invention relates to any one of the aforementioned compounds and attendant definitions, wherein Y is —C(R¹)₂—.

In certain embodiments, the present invention relates to any one of the aforementioned compounds and attendant definitions, wherein Y is —CH₂—.

In certain embodiments, the present invention relates to any one of the aforementioned compounds and attendant definitions, wherein Y is —O—. For examples of 4-oxa-analogs of the muscarinic agonist 2-ethyl-8-methyl-2,8-diazaspiro[4,5]decane-1,3-dione, see *J. Med. Chem.* 1993, 36, 2292, which is hereby incorporated by reference.

In certain embodiments, the present invention relates to any one of the aforementioned compounds and attendant definitions, wherein R¹ is hydrogen.

In certain embodiments, the present invention relates to any one of the aforementioned compounds and attendant definitions, wherein m is 1; and n is 2.

In certain embodiments, the present invention relates to any one of the aforementioned compounds and attendant definitions, wherein m is 1; and n is 3.

In certain embodiments, the present invention relates to any one of the aforementioned compounds and attendant definitions, wherein m is 2; and n is 2.

In certain embodiments, the present invention relates to any one of the aforementioned compounds and attendant definitions, wherein X is —O—; Y is —CH$_2$—; R$^1$ is hydrogen; m is 2; and n is 2.

In certain embodiments, the present invention relates to any one of the aforementioned compounds and attendant definitions, wherein R$^2$ is unsubstituted alkyl.

In certain embodiments, the present invention relates to any one of the aforementioned compounds and attendant definitions, wherein R$^2$ is —CH$_3$, —CH$_2$CH$_3$, —CH$_2$CH$_2$CH$_3$, or —CH(CH$_3$)CH$_3$.

In certain embodiments, the present invention relates to any one of the aforementioned compounds and attendant definitions, wherein R$^2$ is alkyl substituted with —F, —Cl, —Br or —I.

In certain embodiments, the present invention relates to any one of the aforementioned compounds and attendant definitions, wherein R$^2$ is alkyl substituted with —F.

In certain embodiments, the present invention relates to any one of the aforementioned compounds and attendant definitions, wherein R$^2$ is alkyl substituted with —$^{18}$F.

In certain embodiments, the present invention relates to any one of the aforementioned compounds and attendant definitions, wherein R$^2$ is —CH$_2$CH$_2$$^{18}$F or —CH$_2$CH$^{18}$FCH$_3$ In certain embodiments, the present invention relates to any one of the aforementioned compounds and attendant definitions, wherein X is —O—; Y is —CH$_2$—; R$^1$ is hydrogen; m is 2; n is 2; and R$^2$ is alkyl substituted with —F, —Cl, —Br or —I.

In certain embodiments, the present invention relates to any one of the aforementioned compounds and attendant definitions, wherein X is —O—; Y is —CH$_2$—; R$^1$ is hydrogen; m is 2; n is 2; and R$^2$ is alkyl substituted with —F.

In certain embodiments, the present invention relates to any one of the aforementioned compounds and attendant definitions, wherein X is —O—; Y is —CH$_2$—; R$^1$ is hydrogen; m is 2; n is 2; and R$^2$ is alkyl substituted with —$^{18}$F.

In certain embodiments, the present invention relates to any one of the aforementioned compounds and attendant definitions, wherein X is —O—; Y is —CH$_2$—; R$^1$ is hydrogen; m is 2; n is 2; and R$^2$ is —CH$_2$CH$_2$$^{18}$F or —CH$_2$CH$^{18}$FCH$_3$ In certain embodiments, the present invention relates to any one of the aforementioned compounds and attendant definitions, wherein L is R$^3$.

In certain embodiments, the present invention relates to any one of the aforementioned compounds and attendant definitions, wherein L is R$^3$; and R$^3$ is alkyl.

In certain embodiments, the present invention relates to any one of the aforementioned compounds and attendant definitions, wherein L is R$^3$; and R$^3$ is —CH$_3$.

In certain embodiments, the present invention relates to any one of the aforementioned compounds and attendant definitions, wherein X is —O—; Y is —CH$_2$—; R$^1$ is hydrogen; m is 2; n is 2; R$^2$ is alkyl substituted with —F, —Cl, —Br or —I; L is R$^3$; and R$^3$ is alkyl.

In certain embodiments, the present invention relates to any one of the aforementioned compounds and attendant definitions, wherein X is —O—; Y is —CH$_2$—; R$^1$ is hydrogen; m is 2; n is 2; R$^2$ is alkyl substituted with —F; L is R$^3$; and R$^3$ is alkyl.

In certain embodiments, the present invention relates to any one of the aforementioned compounds and attendant definitions, wherein X is —O—; Y is —CH$_2$—; R$^1$ is hydrogen; m is 2; n is 2; R$^2$ is alkyl substituted with —$^{18}$F; L is R$^3$; and R$^3$ is alkyl.

In certain embodiments, the present invention relates to any one of the aforementioned compounds and attendant definitions, wherein X is —O—; Y is —CH$_2$—; R$^1$ is hydrogen; m is 2; n is 2; R$^2$ is —CH$_2$CH$_2$$^{18}$F or —CH$_2$CH$^{18}$FCH$_3$; L is R$^3$; and R$^3$ is —CH$_3$.

One aspect of the invention relates to a fluorinated 2,8-diazaspiro[4,5]decane-1,3-dione compound, or pharmaceutically acceptable salt thereof.

One aspect of the invention relates to a $^{18}$F-fluorinated 2,8-diazaspiro[4,5]decane-1,3-dione compound, or a pharmaceutically acceptable salt thereof.

One aspect of the present invention relates to any one of the aforementioned compounds and attendant definitions, wherein the compound is [F-18]-N-2-fluoroethyl-2,8-diazaspiro[4,5]decane-1,3-dione or [F-18]-N-2-fluoroethyl-2,8-diazaspiro[4,5]decane-1,3-dione.

In certain embodiments, the present invention relates to any one of the aforementioned compounds and attendant definitions, wherein L is —C(=O)R$^3$, —C(=O)[CH$_2$]$_p$R$^3$, —C(=O)[CH$_2$]$_p$C(=O)R$^3$, or —[CH$_2$]$_p$C(=O)R$^3$.

In certain embodiments, the present invention relates to any one of the aforementioned compounds and attendant definitions, wherein L is —C(=O)R$^3$ or —C(=O)CH$_2$CH$_2$C(=O)R$^3$.

In certain embodiments, the present invention relates to any one of the aforementioned compounds and attendant definitions, R$^3$ is

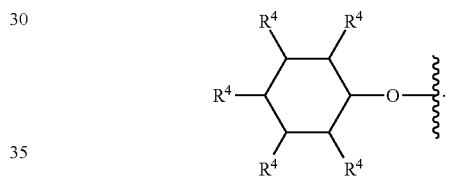

In certain embodiments, the present invention relates to any one of the aforementioned compounds and attendant definitions, R$^3$ is

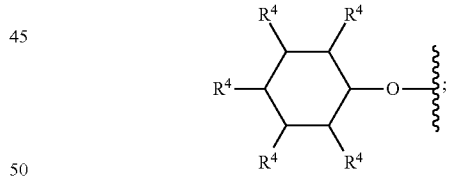

and R$^4$ is —H, —F, —Cl, —Br, —I, or —OR$^5$.

In certain embodiments, the present invention relates to any one of the aforementioned compounds and attendant definitions, R$^3$ is

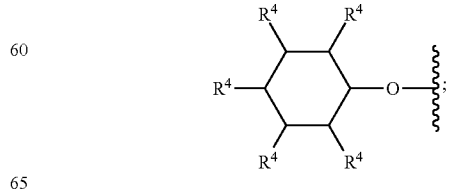

and R$^4$ is —OR$^5$.

In certain embodiments, the present invention relates to any one of the aforementioned compounds and attendant definitions, $R^3$ is

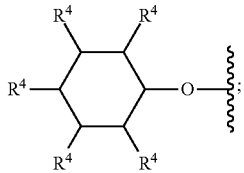

and $R^4$ is —OH.

In certain embodiments, the present invention relates to any one of the aforementioned compounds and attendant definitions, $R^3$ is

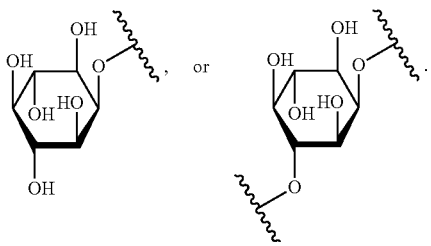

In certain embodiments, the present invention relates to any one of the aforementioned compounds and attendant definitions, wherein L is —C(=O)$R^3$, —C(=O)[CH$_2$]$_p$$R^3$, —C(=O)[CH$_2$]$_p$C(=O)$R^3$, or —[CH$_2$]$_p$C(=O)$R^3$; and $R^3$ is

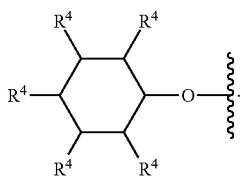

In certain embodiments, the present invention relates to any one of the aforementioned compounds and attendant definitions, wherein L is —C(=O)$R^3$, —C(=O)[CH$_2$]$_p$$R^3$, —C(=O)[CH$_2$]$_p$C(=O)$R^3$, or —[CH$_2$]$_p$C(=O)$R^3$; $R^3$ is

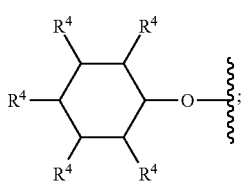

and $R^4$ is —OR$^5$.

In certain embodiments, the present invention relates to any one of the aforementioned compounds and attendant definitions, wherein L is —C(=O)$R^3$; and $R^3$ is

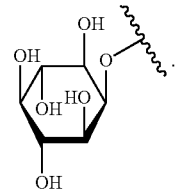

In certain embodiments, the present invention relates to any one of the aforementioned compounds and attendant definitions, wherein L is —C(=O)CH$_2$CH$_2$C(=O)$R^3$; and $R^3$ is

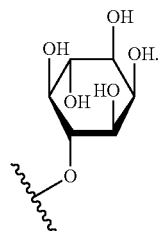

In certain embodiments, the present invention relates to any one of the aforementioned compounds and attendant definitions, wherein X is —O—; Y is —CH$_2$—; $R^1$ is hydrogen; m is 2; n is 2; $R^2$ is alkyl substituted with —$^{18}$F; L is —C(=O)$R^3$, —C(=O)[CH$_2$]$_p$$R^3$, —C(=O)[CH$_2$]$_p$C(=O)$R^3$, or —[CH$_2$]$_p$C(=O)$R^3$; and $R^3$ is

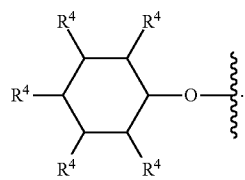

In certain embodiments, the present invention relates to any one of the aforementioned compounds and attendant definitions, wherein X is —O—; Y is —CH$_2$—; $R^1$ is hydrogen; m is 2; n is 2; $R^2$ is alkyl substituted with —$^{18}$F; L is —C(=O)$R^3$, —C(=O)[CH$_2$]$_p$$R^3$, —C(=O)[CH$_2$]$_p$C(=O)$R^3$, or —[CH$_2$]$_p$C(=O)$R^3$; $R^3$ is

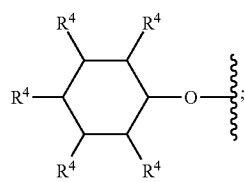

and $R^4$ is —OR$^5$.

In certain embodiments, the present invention relates to any one of the aforementioned compounds and attendant definitions, wherein X is —O—; Y is —CH$_2$—; $R^1$ is hydro gen; m is 2; n is 2; $R^2$ is —$CH_2CH_2^{18}F$ or —$CH_2CH^{18}FCH_3$; L is —$C(=O)R^3$; and $R^3$ is

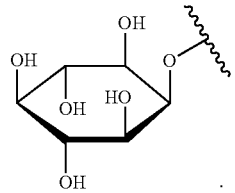

In certain embodiments, the present invention relates to any one of the aforementioned compounds and attendant definitions, wherein X is —O—; Y is —$CH_2$—; $R^1$ is hydrogen; m is 2; n is 2; $R^2$ is —$CH_2CH_2^{18}F$ or —$CH_2CH^{18}FCH_3$; and $R^3$ is

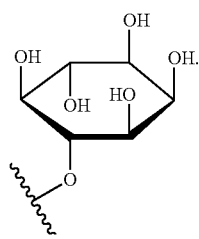

In certain embodiments, the present invention relates to any one of the aforementioned compounds and attendant definitions, $R^3$ is

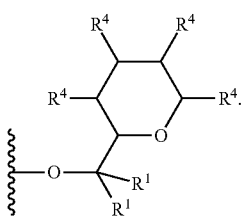

In certain embodiments, the present invention relates to any one of the aforementioned compounds and attendant definitions, $R^3$ is

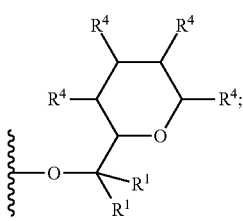

and $R^4$ is —H, —F, —Cl, —Br, —I, or —$OR^5$.

In certain embodiments, the present invention relates to any one of the aforementioned compounds and attendant definitions, $R^3$ is

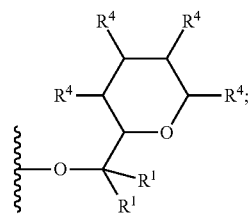

and $R^4$ is —$OR^5$.

In certain embodiments, the present invention relates to any one of the aforementioned compounds and attendant definitions, $R^3$ is

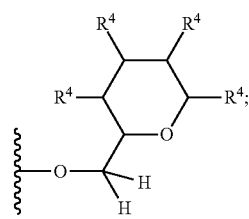

and $R^4$ is —OH.

In certain embodiments, the present invention relates to any one of the aforementioned compounds and attendant definitions, $R^3$ is

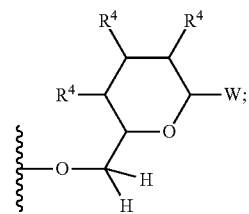

W is —F, —Cl, —Br or —I; and $R^4$ is —$OR^5$.

In certain embodiments, the present invention relates to any one of the aforementioned compounds and attendant definitions, $R^3$ is

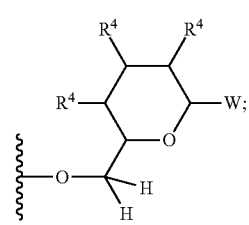

W is —F; and $R^4$ is —$OR^5$.

In certain embodiments, the present invention relates to any one of the aforementioned compounds and attendant definitions, $R^3$ is

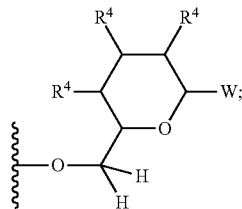

W is $-^{18}F$; and $R^4$ is —OH.

In certain embodiments, the present invention relates to any one of the aforementioned compounds and attendant definitions, wherein X is —O—; Y is —CH$_2$—; $R^1$ is hydrogen; m is 2; n is 2; $R^2$ is unsubstituted alkyl or alkyl substituted with —F, —Cl, —Br, or —I; L is —C(=O)$R^3$, —C(=O)[CH$_2$]$_p$$R^3$, —C(=O)[CH$_2$]$_p$C(=O)$R^3$, or —[CH$_2$]$_p$C(=O)$R^3$; and $R^3$ is

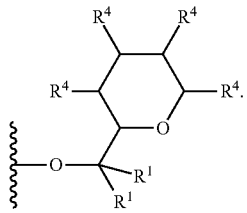

In certain embodiments, the present invention relates to any one of the aforementioned compounds and attendant definitions, wherein X is —O—; Y is —CH$_2$—; $R^1$ is hydrogen; m is 2; n is 2; $R^2$ is alkyl; L is —C(=O)$R^3$ or —C(=O)[CH$_2$]$_p$C(=O)$R^3$; $R^3$ is

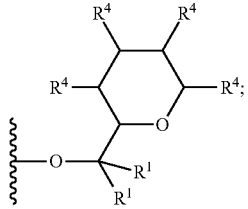

and $R^4$ is —H, —F, —Cl, —Br, —I, or —OR$^5$.

In certain embodiments, the present invention relates to any one of the aforementioned compounds and attendant definitions, wherein X is —O—; Y is —CH$_2$—; $R^1$ is hydrogen; m is 2; n is 2; $R^2$ is unsubstituted alkyl or alkyl substituted with —F, —Cl, —Br, or —I; L is —C(=O)CH$_2$CH$_2$C(=O)$R^3$; $R^3$ is

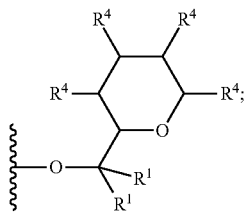

and $R^4$ is —OR$^5$.

In certain embodiments, the present invention relates to any one of the aforementioned compounds and attendant definitions, wherein X is —O—; Y is —CH$_2$—; $R^1$ is hydrogen; m is 2; n is 2; $R^2$ is alkyl substituted with —F; L is —C(=O)CH$_2$CH$_2$C(=O)$R^3$; $R^3$ is

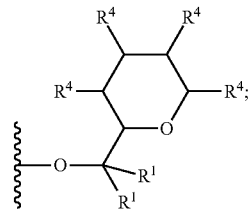

and $R^4$ is —OH.

In certain embodiments, the present invention relates to any one of the aforementioned compounds and attendant definitions, wherein X is —O—; Y is —CH$_2$—; $R^1$ is hydrogen; m is 2; n is 2; $R^2$ is alkyl substituted with —$^{18}$F; L is —C(=O)CH$_2$CH$_2$C(=O)$R^3$; $R^3$ is

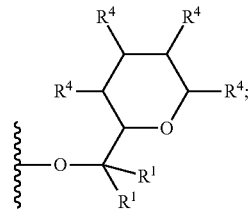

and $R^4$ is —OH.

In certain embodiments, the present invention relates to any one of the aforementioned compounds and attendant definitions, wherein X is —O—; Y is —CH$_2$—; $R^1$ is hydrogen; m is 2; n is 2; $R^2$ is —CH$_2$CH$_2$$^{18}$F or —CH$_2$CH$^{18F}$CH$_3$; L is —C(=O)CH$_2$CH$_2$C(=O)$R^3$; $R^3$ is

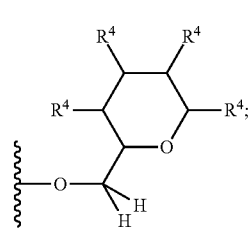

and $R^4$ is —OH.

In certain embodiments, the present invention relates to any one of the aforementioned compounds and attendant definitions, wherein X is —O—; Y is —CH$_2$—; $R^1$ is hydrogen; m is 2; n is 2; $R^2$ is; L is —C(=O)$R^3$ or —C(=O)[CH$_2$]$_p$C(=O)—; $R^3$ is

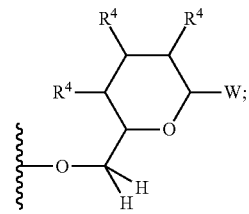

W is —F; and $R^4$ is —OR$^5$.

In certain embodiments, the present invention relates to any one of the aforementioned compounds and attendant definitions, wherein X is —O—; Y is —CH$_2$—; R$^1$ is hydrogen; m is 2; n is 2; R$^2$ is unsubstituted alkyl; L is —C(=O)R$^3$ or —C(=O)CH$_2$CH$_2$C(=O)—; R$^3$ is

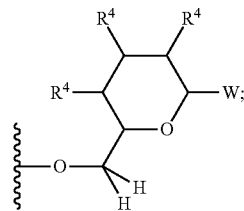

W is —$^{18}$F; and R$^4$ is —OH.

In certain embodiments, the present invention relates to any one of the aforementioned compounds and attendant definitions, wherein the compound comprises a radioimaging agent.

In certain embodiments, the present invention relates to any one of the aforementioned compounds and attendant definitions, wherein R$^1$ comprises the radioimaging agent.

In certain embodiments, the present invention relates to any one of the aforementioned compounds and attendant definitions, wherein R$^1$ comprises the radioimaging agent; and the radioimaging agent is $^{18}$F.

In certain embodiments, the present invention relates to any one of the aforementioned compounds and attendant definitions, wherein R$^2$ comprises the radioimaging agent.

In certain embodiments, the present invention relates to any one of the aforementioned compounds and attendant definitions, wherein R$^2$ comprises the radioimaging agent; and the radioimaging agent is $^{18}$F.

In certain embodiments, the present invention relates to any one of the aforementioned compounds and attendant definitions, wherein R$^3$ comprises the radioimaging agent.

In certain embodiments, the present invention relates to any one of the aforementioned compounds and attendant definitions, wherein R$^3$ comprises the radioimaging agent; and the radioimaging agent is $^{18}$F.

In certain embodiments, the present invention relates to any one of the aforementioned compounds and attendant definitions, wherein R$^4$ comprises the radioimaging agent.

In certain embodiments, the present invention relates to any one of the aforementioned compounds and attendant definitions, wherein R$^4$ comprises the radioimaging agent; and the radioimaging agent is $^{18}$F.

One aspect of the invention relates to a compound, or a pharmaceutically acceptable salt thereof, represented by formula II:

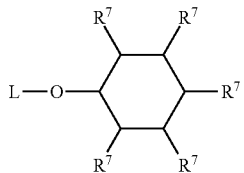

wherein, independently for each occurrence,

L is —H, —C(=O)R$^3$, —C(=O)[C(R$^1$)$_2$]$_p$R$^3$, —C(=O)[C(R$^1$)$_2$]$_p$C(=O)R$^3$, —[C(R$^1$)$_2$]$_p$C(=O)R$^3$, —[C(R$^1$)$_2$]$_p$R$^3$, —C$_{1-10}$alkylene]R$^3$, —C(=O)[C$_{1-10}$alkylene]R$^3$, —[C$_{1-10}$alkylene]C(=O)R$^3$ or —C(=O)[C$_{1-10}$alkylene]C(=O)R$^3$;

R$^1$ is hydrogen, halo, azido, alkyl, haloalkyl, perhaloalkyl, fluoroalkyl, perfluoroalkyl, aralkyl, alkenyl, alkynyl, cycloalkyl, heterocyclyl, aryl, heteroaryl, aralkyl, heteroaralkyl, hydroxy, alkoxy, aryloxy, heteroaryloxy, aralkyloxy, heteroaralkyloxy, amino, alkylamino, arylamino, acylamino, heteroarylamino, nitro, sulfhydryl, imino, amido, phosphonate, phosphinate, acyl, carboxyl, oxycarbonyl, acyloxy, silyl, thioether, sulfo, sulfonate, sulfonyl, sulfonamido, formyl, cyano, or isocyano;

R$^3$ is

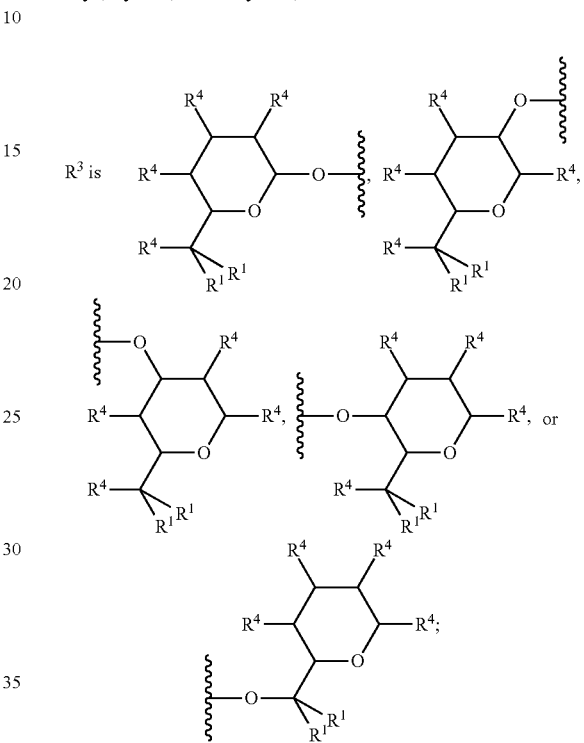

R$^4$ is hydrogen, halo, azido, alkyl, haloalkyl, perhaloalkyl, fluoroalkyl, perfluoroalkyl, aralkyl, alkenyl, alkynyl, cycloalkyl, heterocyclyl, aryl, heteroaryl, aralkyl, heteroaralkyl, hydroxy, alkoxy, aryloxy, heteroaryloxy, aralkyloxy, heteroaralkyloxy, amino, alkylamino, arylamino, acylamino, heteroarylamino, nitro, sulfhydryl, imino, amido, phosphonate, phosphinate, acyl, carboxyl, oxycarbonyl, acyloxy, silyl, thioether, sulfo, sulfonate, sulfonyl, sulfonamido, formyl, cyano, isocyano, —OR$^5$, —SR$^5$, —N(R$^5$)$_2$, —(C(R$^1$)$_2$)$_q$C(R$^1$)$_3$ or a chelating structure;

R$^5$ is hydrogen, alkyl, heteroalkyl, cycloalkyl, heterocycloalkyl, aryl, heteroaryl, aralkyl, heteroaralkyl, acyl, —(C(R$^1$)$_2$)$_q$C(R$^1$)$_3$ or a chelating structure.

R$^7$ is hydrogen, halo, azido, alkyl, haloalkyl, perhaloalkyl, fluoroalkyl, perfluoroalkyl, aralkyl, alkenyl, alkynyl, cycloalkyl, heterocyclyl, aryl, heteroaryl, aralkyl, heteroaralkyl, hydroxy, alkoxy, aryloxy, heteroaryloxy, aralkyloxy, heteroaralkyloxy, amino, alkylamino, arylamino, acylamino, heteroarylamino, nitro, sulfhydryl, imino, amido, phosphonate, phosphinate, acyl, carboxyl, oxycarbonyl, acyloxy, silyl, thioether, sulfo, sulfonate, sulfonyl, sulfonamido, formyl, cyano, isocyano, —OR$^5$, —SR$^5$, —N(R$^5$)$_2$, —(C(R$^1$)$_2$)$_q$C(R$^1$)$_3$ or a chelating structure;

p is 1-10 inclusive; and q is 0-10 inclusive;

provided that when L is —H, one R$^7$ is fluoro; and the other R$^7$ are hydroxy, alkoxy, aryloxy, heteroaryloxy, aralkyloxy, or heteroaralkyloxy.

In certain embodiments, the present invention relates to any one of the aforementioned compounds and attendant definitions, wherein said compound comprises at least one $^{18}F$, $^{76}Br$, $^{77}Br$, $^{123}I$, $^{124}I$ or $^{125}I$.

In certain embodiments, the present invention relates to any one of the aforementioned compounds and attendant definitions, wherein said compound comprises at least one $^{18}F$.

In certain embodiments, the present invention relates to any one of the aforementioned compounds and attendant definitions, wherein said compound comprises only one chelating structure.

In certain embodiments, the present invention relates to any one of the aforementioned compounds and attendant definitions, wherein said compound comprises only one chelating structure; and $^{99m}Tc$, $^{68}Cu$, $^{64}Cu$ or $^{68}Ga$ chelated to the chelating structure.

In certain embodiments, the present invention relates to any one of the aforementioned compounds and attendant definitions, wherein L is —C(=O)$R^3$ or —C(=O)[C($R^1$)$_2$]$_p$C(=O)$R^3$—.

In certain embodiments, the present invention relates to any one of the aforementioned compounds and attendant definitions, wherein L is —C(=O)$R^3$.

In certain embodiments, the present invention relates to any one of the aforementioned compounds and attendant definitions, wherein L is —C(=O)[CH$_2$]$_p$C(=O)$R^3$.

In certain embodiments, the present invention relates to any one of the aforementioned compounds and attendant definitions, wherein L is —C(=O)CH—$_2$CH$_2$C(=O)$R^3$.

In certain embodiments, the present invention relates to any one of the aforementioned compounds and attendant definitions, wherein $R^7$ is —H, —F, —Cl, —Br, —I, or —O$R^5$.

In certain embodiments, the present invention relates to any one of the aforementioned compounds and attendant definitions, wherein $R^7$ is —H, —F, —Cl, —Br, —I, or —OH.

In certain embodiments, the present invention relates to any one of the aforementioned compounds and attendant definitions, wherein $R^7$ is —F or —OH.

In certain embodiments, the present invention relates to any one of the aforementioned compounds and attendant definitions, wherein $R^7$ is —$^{18}F$ or —OH; provided that only one $R^7$ is —$^{18}F$.

In certain embodiments, the present invention relates to any one of the aforementioned compounds and attendant definitions, wherein L is —C(=O)$R^3$ or —C(=O)[C($R^1$)$_2$]$_p$C(=O)$R^3$; and $R^7$ is —H, —F, —Cl, —Br, —I, or —O$R^5$.

In certain embodiments, the present invention relates to any one of the aforementioned compounds and attendant definitions, wherein L is —C(=O)$R^3$; and $R^7$ is —H, —F, —Cl, —Br, —I, or —O$R^5$.

In certain embodiments, the present invention relates to any one of the aforementioned compounds and attendant definitions, wherein L is —C(=O)[CH$_2$]$_p$C(=O)$R^3$; and $R^7$ is —H, —F, —Cl, —Br, —I, or —O$R^5$.

In certain embodiments, the present invention relates to any one of the aforementioned compounds and attendant definitions, wherein L is —C(=O)$R^3$; and $R^7$ is —OH.

In certain embodiments, the present invention relates to any one of the aforementioned compounds and attendant definitions, wherein L is —C(=O)CH—$_2$CH$_2$C(=O)$R^3$; and $R^7$ is OH.

In certain embodiments, the present invention relates to any one of the aforementioned compounds and attendant definitions, wherein L is —C(=O)$R^3$; and $R^7$ is $R^7$ is —F or —OH; provided that only one $R^7$ is —F.

In certain embodiments, the present invention relates to any one of the aforementioned compounds and attendant definitions, wherein L is —C(=O)CH—$_2$CH$_2$C(=O)$R^3$; and $R^7$ is —F or —OH; provided that only one $R^7$ is —F.

In certain embodiments, the present invention relates to any one of the aforementioned compounds and attendant definitions, wherein L is —C(=O)$R^3$; and $R^7$ is $R^7$ is —$^{18}F$ or —OH; provided that only one $R^7$ is —$^{18}F$.

In certain embodiments, the present invention relates to any one of the aforementioned compounds and attendant definitions, wherein L is —C(=O)CH—$_2$CH$_2$C(=O)$R^3$; and $R^7$ is —$^{18}F$ or —OH; provided that only one $R^7$ is —$^{18}F$.

In certain embodiments, the present invention relates to any one of the aforementioned compounds and attendant definitions, wherein $R^3$ is In certain embodiments, the present invention relates to any one of the aforementioned compounds and attendant definitions, $R^3$ is and $R^4$ is —H, —F, —Cl, —Br, —I, or —O$R^5$.

In certain embodiments, the present invention relates to any one of the aforementioned compounds and attendant definitions, $R^3$ is and $R^4$ is —O$R^5$.

In certain embodiments, the present invention relates to any one of the aforementioned compounds and attendant definitions, $R^3$ is and $R^4$ is —OH.

In certain embodiments, the present invention relates to any one of the aforementioned compounds and attendant definitions, $R^3$ is

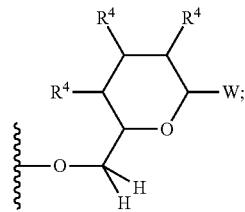

W is —F, —Cl, —Br or —I; and $R^4$ is —$OR^5$.

In certain embodiments, the present invention relates to any one of the aforementioned compounds and attendant definitions, $R^3$ is

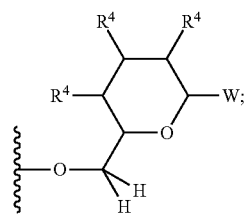

W is —F; and $R^4$ is —$OR^5$.

In certain embodiments, the present invention relates to any one of the aforementioned compounds and attendant definitions, $R^3$ is

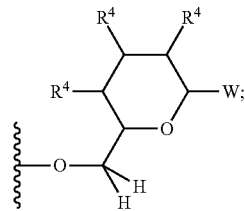

W is —$^{18}$F; and $R^4$ is —OH.

In certain embodiments, the present invention relates to any one of the aforementioned compounds and attendant definitions, wherein L is —C(=O)$R^3$ or —C(=O)[C($R^1$)$_2$]$_p$C(=O)$R^3$; $R^7$ is —H, —F, —Cl, —Br, —I, or —$OR^5$; and $R^3$ is

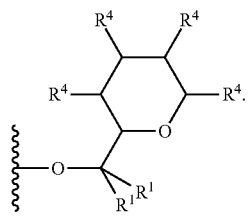

In certain embodiments, the present invention relates to any one of the aforementioned compounds and attendant definitions, wherein L is —C(=O)$R^3$ or —C(=O)[C($R^1$)$_2$]$_p$C(=O)$R^3$; $R^7$ is —H, —F, —Cl, —Br, —I, or —$OR^5$; and $R^3$ is

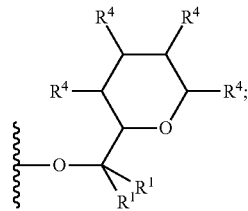

and $R^4$ is —H, —F, —Cl, —Br, —I, or —$OR^5$.

In certain embodiments, the present invention relates to any one of the aforementioned compounds and attendant definitions, wherein L is —C(=O)$R^3$ or —C(=O)[C($R^1$)$_2$]$_p$C(=O)$R^3$; $R^7$ is —H, —F, —Cl, —Br, —I, or —$OR^5$; $R^3$ is

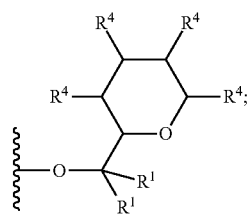

and $R^4$ is –$OR^5$.

In certain embodiments, the present invention relates to any one of the aforementioned compounds and attendant definitions, wherein L is —C(=O)$R^3$ or —C(=O)[C($R^1$)$_2$]$_p$C(=O)$R^3$; $R^7$ is —H, —F, —Cl, —Br, —I, or —$OR^5$; $R^3$ is

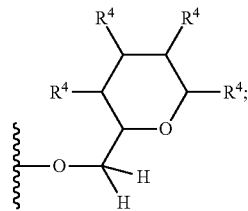

and $R^4$ is —OH.

In certain embodiments, the present invention relates to any one of the aforementioned compounds and attendant definitions, wherein L is —C(=O)$R^3$ or —C(=O)[C($R^1$)$_2$]$_p$C(=O)$R^3$; $R^7$ is —H, —F, —Cl, —Br, —I, or —$OR^5$; $R^3$ is

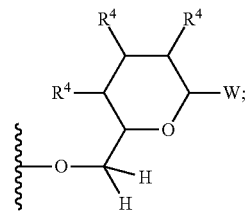

W is —F, —Cl, —Br or —I; and $R^4$ is —$OR^5$.

In certain embodiments, the present invention relates to any one of the aforementioned compounds and attendant definitions, wherein L is —C(=O)$R^3$ or —C(=O)[C($R^1$)$_2$]$_p$C(=O)$R^3$; $R^7$ is —H, —F, —Cl, —Br, —I, or —$OR^5$; $R^3$ is

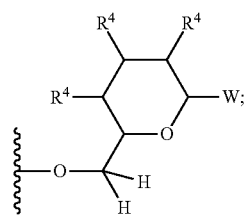

W is —F; and R$^4$ is —OR$^5$.

In certain embodiments, the present invention relates to any one of the aforementioned compounds and attendant definitions, wherein L is —C(=O)R$^3$ or —C(=O)[C(R$^1$)$_2$]$_p$C(=O)R$^3$; R$^7$ is —H, —F, —Cl, —Br, —I, or —OR$^5$; R$^3$ is

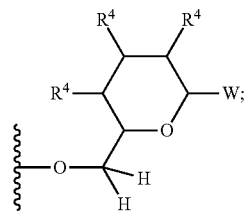

W is —$^{18}$F; and R$^4$ is —OH.

In certain embodiments, the present invention relates to any one of the aforementioned compounds and attendant definitions, wherein L is —H, one R$^7$ is fluoro; and the other R$^7$ are hydroxy, alkoxy, aryloxy, heteroaryloxy, aralkyloxy, or heteroaralkyloxy.

In certain embodiments, the present invention relates to any one of the aforementioned compounds and attendant definitions, wherein the compound is 1-deoxy-1-fluoro-scyllo-inostiol or 1-deoxy-1-fluoro-myo-inositol.

In certain embodiments, the present invention relates to any one of the aforementioned compounds and attendant definitions, wherein the compound comprises a radioimaging agent.

In certain embodiments, the present invention relates to any one of the aforementioned compounds and attendant definitions, wherein R$^1$ comprises the radioimaging agent.

In certain embodiments, the present invention relates to any one of the aforementioned compounds and attendant definitions, wherein R$^1$ comprises the radioimaging agent; and the radioimaging agent is $^{18}$F.

In certain embodiments, the present invention relates to any one of the aforementioned compounds and attendant definitions, wherein R$^4$ comprises the radioimaging agent.

In certain embodiments, the present invention relates to any one of the aforementioned compounds and attendant definitions, wherein R$^4$ comprises the radioimaging agent; and the radioimaging agent is $^{18}$F.

In certain embodiments, the present invention relates to any one of the aforementioned compounds and attendant definitions, wherein R$^7$ comprises the radioimaging agent.

In certain embodiments, the present invention relates to any one of the aforementioned compounds and attendant definitions, wherein R$^7$ comprises the radioimaging agent; and the radioimaging agent is $^{18}$F.

One aspect of the present invention relates to a pharmaceutical composition comprising a pharmaceutically acceptable carrier and a compound, or a pharmaceutically acceptable form thereof; wherein the compound is any of the compound described herein.

In certain embodiments, the present invention relates to any one of the aforementioned pharmaceutical composition and attendant definitions, wherein said compound is a compound of formula I or II and attendant definitions thereto.

One aspect of the present invention relates to a method for amyloid imaging a subject suffering from an amylodiosis-associated pathological condition, or treating a subject suffering fromamylodiosis-associated pathological condition, comprising the step of:

administering a compound, or a composition comprising a pharmaceutically acceptable carrier and the compound or a pharmaceutically acceptable form thereof, wherein the compound is represented by any of the compound described herein.

In certain embodiments, the present invention relates to any one of the aforementioned methods and attendant definitions, wherein said compound is a compound of formula I or II and attendant definitions thereto.

In certain embodiments, the present invention relates to any one of the aforementioned methods and attendant definitions, wherein said amylodiosis-associated pathological condition is Alzheimer's disease.

In certain embodiments, the present invention relates to any one of the aforementioned methods and attendant definitions, wherein said compound comprises at least one $^{18}$F, $^{76}$Br, $^{77}$Br, $^{123}$I, $^{124}$I or $^{125}$I.

In certain embodiments, the present invention relates to any one of the aforementioned methods and attendant definitions, wherein the compound is

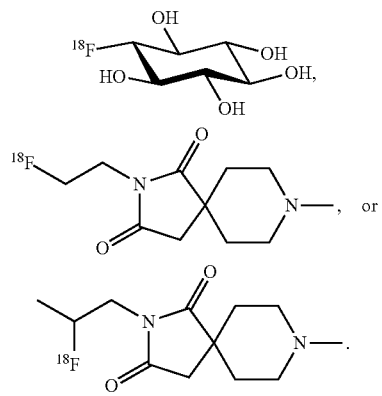

One aspect of the present invention relates to a method for treating a subject suffering from an amylodiosis-associated pathological condition, comprising the step of:

administering a compound, or a composition comprising a pharmaceutically acceptable carrier and the compound or a pharmaceutically acceptable form thereof, wherein the compound is represented by any of the compounds described herein.

In certain embodiments, the present invention relates to any one of the aforementioned methods and attendant definitions, wherein said compound is a compound of formula I or II and attendant definitions thereto.

In certain embodiments, the present invention relates to any one of the aforementioned methods and attendant definitions, wherein said amylodiosis-associated pathological condition is Alzheimer's disease.

In certain embodiments, the present invention relates to any one of the aforementioned methods and attendant definitions, wherein said treatment inhibits the formation of plaque.

In certain embodiments, the present invention relates to any one of the aforementioned methods and attendant definitions, wherein said compound is a combination of RS-86 and inositol, a combination of RS-86 and glucose, a combination of inositol and glucose, or a disaccharide comprising inositiol and glucose.

In certain embodiments, the present invention relates to any one of the aforementioned methods and attendant definitions, wherein said combination shows increased uptake over one or both of the constituents thereof.

In certain embodiments, the present invention relates to any one of the aforementioned methods and attendant definitions, wherein said combination shows increased uptake over one or both of the constituents thereof, in cells of the blood, heart, lung, liver, spleen, kidney, adrenal gland, stomach, gi tract, gonads, skeletal muscle, bone, or brain.

In certain embodiments, the present invention relates to any one of the aforementioned methods and attendant definitions, wherein said combination shows increased uptake over one or both of the constituents thereof, in the brain.

In certain embodiments, the present invention relates to any one of the aforementioned methods and attendant definitions, wherein said compound is fluoronated.

In certain embodiments, the present invention relates to any one of the aforementioned methods and attendant definitions, wherein the compound is

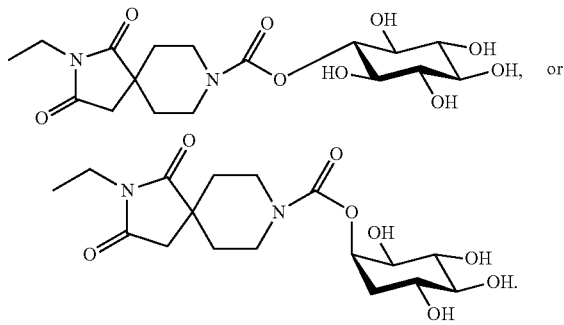

EXEMPLIFICATION

It should be understood that the above-described embodiments and the following examples are given by way of illustration, not limitation. Various changes and modifications within the scope of the present invention will become apparent to those skilled in the art from the present description.
General Reaction Materials and Methods of Analysis All reactions were carried out in dry glassware (oven at 150° C. for 12 hrs) unless otherwise noted and a steady stream of dry $N_2$ gas was used to prevent moisture-air off the reaction system. All chemicals and solvents for moisture-sensitive reactions were purchased from Aldrich chemical company and used as supplied. Ethyl ether was distilled from sodium-benzophenone immediately prior to use. Dichloromethane was distilled from CaH or $P_2O_5$ prior to use. DMF was distilled under reduced pressure onto activated 4 angstrom molecular sieves or purchased as dry solvent for immediate use. Syringes possessing Teflon or rubber seals/plungers were dried (24 h) using an evacuated Abderhalden drying apparatus at 56° C. (acetone) with KOH as the desiccant and the same Abderhalden drying apparatus at 64° C. (methyl alcohol) with $P_2O_5$ was used for sample drying purpose. Reactions carried out at −50° C. employed the frozen slurry of 50% $CaCl_2$ solution with powdered dry-ice. $^1H$ NMR spectra were recorded on a 300 MHz Varian Mercury instrument and reported in parts per million (ppm), with residual $CDCl_3$ referenced at 7.26 ppm and $Me_4Si$ at 0.00 ppm. Multiplicity, coupling constant (Hz), and proton count follow each peak assignment. Elemental analyses were performed by Robertson Laboratories, Madison, N.J., and were within +/−0.4% of theoretical values unless otherwise indicated. Analytic polyester TLC plates were purchased from Aldrich (Silica gel thickness: 250 μm, pore size 60 angstroms, 20×20 cm, Fluorescent indicator, Cat. No. Z122785). TLC plates were visualized using a 254 nm/366 nm UV lamp and 5% ethanol solution of phosphomolybdic acid or an iodine/silica gel mixture. Preparative TLC plates were purchased from Sigma-Aldrich (silica gel on glass, 2000 μm, 20×20 cm, fl. Ind. Cat No. Z513040). Chromatographic separations were made using Silia-P Flask silica gel (Silicycle Chemical Division, Quebec, QC, Canada), particle size: 40-63 μm, 60 angstroms. HRMS determinations were done by Molecular Biology Core Facilities, DFCI, MA in the electron-impact (EI) or fast-atom bombardment (FAB) mode.

Example 1

FIG. 3 depicts one approach to the synthesis of two novel fluorinated 2,8-diazaspiro[4,5]decane-1,3-dione derivatives. Synthetic protocols for the synthesis of the compounds depicted in FIG. 3 are presented below.

[A] Synthesis of ethyl (1-methyl-4-piperidylidene)cyanoacetate (1; FIG. 3). See U.S. Pat. No. 3,056,796, hereby incorporated by reference; *Bioorganic & Medicinal Chemistry Letters* 2002, 12, 1103; and *J. Med. Chem.* 2004, 47 (8), 2037. To a stirred solution of 1-methyl-4-piperidone (10.0 g, 88.3 mmol) and ethyl cyanoacetate (13.0 g, 115.2 mmol) in $CH_2Cl_2$ (100 mL) was added $Et_3N$ (17.9 g, 177.0 mmol). Then, crushed 4 angstrom molecular sieves (9.0 g) were added and the mixture was stirred at room temperature overnight. The reaction mixture was filtered through Celite, and the filtrate was concentrated to give the product as a clear red syrup (15 g; yield 82%). $^1$HNMR ($CDCl_3$-d) δ 1.31 (t, 3H, $CH_2CH_3$), 2.28 (s, 3H, N—$CH_3$), 2.50 (t, 2H, $J_{ab}$=5.7 Hz, $CH_2N$), 2.57 (t, 2H, $J_{ab}$=6.0 Hz, $CH_2N$), 2.77 (t, 2H, $J_{ab}$=6.0 Hz, $CH_2C$=C), 3.12 (t, 2H, $J_{ab}$=5.7 Hz, $CH_2C$=C). It was used directly in the following step without further purification.

[B] Synthesis of 1-methyl-4-cyanomethylpiperidine-4-carbonitrile (2; FIG. 3). The ethyl ester 1 (15 g, 72.1 mmol) obtained from previous step was dissolved in ethanol (150 ml). A solution of KCN (28.7 g, 442 mmol) in $H_2O$ (60 mL). The red solution was heated to reflux for 4 h, then solvent was evaporated under the reduced pressure to a dark-red syrup which was extracted with EtOAc (4×100). The combined organic extract was washed with brine, dried over $MgSO_2$, and concentrated to yield a red clear oil. Chromatography using 10% methanol in $CH_2Cl_2$ furnished pure dinitrile compound (8.8 g; yield 74.9%). $^1$HNMR ($CDCl_3$-d) δ 1.75 (m, 2H, $CH_2N$), 2.06 (d, 2H, $CH_2N$), 2.30 (m, 2H, $CH_2C$=N), 2.33 (s, 3H, $NCH_3$), 2.73 (s, 2H, $CH_2CN$), 2.87 (d, 2H, $CH_2C$=N).

[C] Synthesis of 1-methyl-4-carboxymethylpiperidine-4-carboxylic acid hydrochloride (3; FIG. 3). See *J. Med. Chem.* 2004, 47 (8), 2037. A suspension of dinitrile 2 (14.4 g, 88.3 mmol) in concentrated HCl (250 mL) was refluxed for 36 h. Then the pale yellow solution was concentrated under the reduced pressure to dryness to afford the diacid 3 as an off-white solid, as its hydrochloride salt (19.1 g; yield 91%). $^1$HNMR (DMSO-d6) δ1.92 (t, 2H, $CH_2N$), 2.17 (t, 2H, $CH_2N$), 2.46 (s, 1H, $CH_2CCO_2H$), 2.72 (s, 3H, $NCH_3$), 2.84 (m, 2H, $CH_2CCO_2H$), 3.24 (q, 1H, $CH_2CCO_2H$), 3.33 (s, 2H, $CH_2CO_2H$), 10.88 (m, 2H, COOH).

[D] Synthesis of 8-methyl-2,8-diazaspiro[4,5]decane-1,3-dione (4; FIG. 3). See *J. Med. Chem.* 1988, 31(8), 1598. The diacid HCl 3 (16.4 g, 69 mmol) was dissolved in 30 mL conc. $NH_4OH$ and heated to reflux for 1 hour and then the volatile components of the solution were distilled off at normal pressure, the residue was heated at 250° C. for 5 h. After cooling, the residue was treated with hot water (10 mL), 50% $K_2CO_3$ (28 mL), and using 50% NaOH (1 mL) the pH of the solution was adjusted to 12. Then the mixture was extracted with chloroform (3×100 mL) and concentrated under the reduced pressure to provide a slight brown solid. The crude product was purified by crystallization in 2-propanol to give a yellow crystal (7.6 g; yield 60%). $^1$HNMR (CDCl$_3$-d) δ 1.55 (d, 2H, CH$_2$N), 2.03 (t, 2H, CH$_2$C), 2.12 (t, 2H, CH$_2$N), 2.28 (s, 3H, NCH$_3$), 2.56 (s, 2H, CH$_2$CO), 2.87 (d, 2H, CH$_2$C).

Note: For the preparation of compound 4, the product was easy to decompose and had caused lower yield under the condition cited from literature, higher temperature 230-280° C. in vacuo. The condition was modified by controlling the temperature at 250° C. at the normal pressure to increase the yield from literature 31% to 60%.

[E] Synthesis of 2-(2-hydroxyethyl)-8-methyl-2,8-diazaspiro[4,5]decane-1,3-dione (5; FIG. 3). See *J. Med. Chem.* 1988, 31(8), 1598. A solution of compound 4 (1.8 g, 10 mmol) dissolved in fresh distilled DMF (10 mL) was treated with 95% NaH (0.28 g, 11 mmol) in mineral oil and the mixture was stirred for 1.5 h at 50° C. and then there was added a solution of 2-bromoethanol (1.58 g, 12 mmol) in DMF (6 mL) over the period of 50 min and the mixture was stirred for 4 h at 75 to 80° C. Then the mixture was filtered with 1 g active charcoal carbon and the filtrate was evaporated in vacuo. The residue was extracted with chloroform (3×50 mL) and the precipitated salts were filtered off, the filtrate was filtered through a layer of neutral Al$_2$O$_3$ (activity II). The solvent was evaporated under the reduced pressure to give a colorless semi-solid. The crude product can't be perfectly purified by crystallization with a mixture of 2-propanol:hexanes (20:5). The pure product was obtained as a colorless powder by flash chromatography with 15% methanol in CH$_2$Cl$_2$ (1.12 g; yield 50%). $^1$H NMR (CDCl$_3$-d) δ 1.49 (d, 2H, CH$_2$N), 1.98 (t, 2H, CH$_2$C), 2.08 (t, 2H, CH$_2$N), 2.25 (s, 3H, NCH$_3$), 2.51 (s, 2H, CH$_2$CO), 2.81 (d, 2H, CH$_2$C), 3.63 (t, 2H, NCH$_2$CH$_2$), 3.69 (t, 2H, CH$_2$OH).

Note: In the preparation of spiro-compound 5, using the same purification method provided in literature was failed to obtain a pure product, a need for flash chromatography was required. Elution with 15% methanol in CH$_2$Cl$_2$ afforded a 50% yield that was lower than that (76%) reported in literature. The product has a weak UV absorption so its TLC detection is difficult too. I$_2$/Silical gel was used for chromatography detection of the product.

[F] Synthesis of 2-(2-methanesulfonylethyl)-8-methyl-2,8-diazaspiro[4,5]decane-1,3-done (6; FIG. 3). In a 25-ml round-bottom flask was dissolved compound 5 (0.3 g, 1.3 mmol) in anhydrous dichloromethane (5 mL). To this solution was added triethylamine (0.27 g, 2.6 mmol), the reaction mixture was cooled to 0° C. with an ice-NaCl bath. Methanesulfonyl chloride was added dropwise, and the reaction mixture was stirred under nitrogen for 2 h, allowing the ice bath to expire and stirred at room temperature for 1 h. Then the reaction mixture was diluted with dichloromethane (20 mL), washed with a sat. solution of NaHCO$_3$, then brine, dried over MgSO$_4$, and the solvent was evaporated under the reduced pressure to provide a yellow clear oil. The product was purified by flash chromatography eluted with a mixture of 10% methanol in dichloromethane to give a colorless clear syrup which evaporated under high vacuum to obtain a colorless semi-solid (144 mg; yield 36%). $^1$HNMR (CDCl$_3$-d) δ1.48 (d, 2H, CH$_2$N), 1.93 (t, 2H, CH$_2$C), 2.05 (t, 2H, CH$_2$N), 2.23 (s, 3H, NCH$_3$), 2.51 (s, 2H, CH$_2$CO), 2.78 (d, 2H, CH$_2$C), 2.94 (s, 3H, CH$_3$SO$_3$), 3.76 (t, 2H, NCH$_2$CH$_2$), 4.34 (t, 2H, CH$_2$OSO$_2$CH$_3$).

[G] Synthesis of 2-(2-hydroxypropyl)-8-methyl-2,8-diazaspiro[4,5]decane-1,3-dione (7; FIG. 3). To a solution of compound 4 (1.8 g, 10 mmol) in DMF (10 mL) was slowly added 95% NaH in mineral oil (0.28 g, 11 mmol), which produced a lot of bubbles and additional DMF (5 mL) was added. The mixture was stirred at 65° C. for 1 h. To the mixture a solution of 1-bromo-2-propanol (1.2 g, 12 mmol) in DMF (6 mL) was added over 80 min until the brown bubbles all dissolved and the mixture became a clear yellow solution, then the temperature of the oil bath was raised up to 70° C. and kept overnight. The mixture was added charcoal carbon (0.1 g) and filtered through a layer of Celite. The filtrate was evaporated to dryness under the reduced pressure and the residue was extracted with chloroform (3×60 mL). The collected chloroform was filtered off the insoluble materials and then filtered through a layer of neutral Al$_2$O$_3$ (activity II). The filtrate was evaporated in the reduced pressure to give a yellow solid. The crude product was purified by crystallization after trituration with a mixture of hexanes and 2-propanol (4:1) to provide a colorless powder (1.3 g; yield 54%). $^1$H NMR (CDCl$_3$-d) δ 1.13 (d, 3H, CH$_3$CH), 1.47 (t, 2H, CH$_2$N), 1.99 (t, 2H, CH$_2$N), 2.08 (t, 2H, CH$_2$C), 2.24 (s, 3H, NCH$_3$), 2.53 (s, 2H, CH$_2$CO), 2.82 (t, 2H, CH$_2$C), 3.48 (d, 2H, NCH$_2$CH), 3.94 (m, 1H, CHOH).

Note: In the preparation of compound 7, the addition of NaH (95%) will cause a large amount of bubbles and heat to be released, so the suggestion is to use a ice bath at the beginning of the reaction, then take it away after finishing the NaH addition. After the overnight reaction, charcoal addition is necessary to remove any conjugation or dehydration by-products and Filtration through Al$_2$O$_3$ layer is to remove possible acidic by-products. Attempts to react compound 4 with propylene oxide and sodium hydride in DMF to prepare the product 7 have been unsuccessful. Although the commercial starting material, 1-bromo-2-propanol, contains 30% of its isomer, 2-bromo-1-propanol, it appears that this isomer did not have any negative effect on the separation of a pure product in the procedure outlined above.

[H] Synthesis of 2-(2-methanesulfonylpropyl)-8-methyl-2,8-diazaspiro[4,5]decane-1,3-done (8; FIG. 3). To a solution of compound 7 (1.3 g, 5.4 mmol) dissolved in freshly distilled CH$_2$Cl$_2$ (20 ml) in an ice-salt bath (0° C.) was added triethylamine (1.09 g, 6.6 mmol) and then methanesulfonyl chloride was added dropwise. The reaction mixture was stirred under nitrogen for 1.5 h, allowing the ice-bath to expire, and stirring continued at room temperature for 1 h. The mixture was diluted with CH$_2$Cl$_2$ (20 mL), and then washed with sat. NaHCO$_3$, brine, and dried over MgSO$_4$. The solution was evaporated under the reduced pressure to give a yellow solid. The crude product was purified by chromatography eluted with 15% methanol in CH$_2$Cl$_2$ to obtain a colorless powder (0.9 g; yield 52%). $^1$H NMR (CDCl$_3$-d) δ 1.40 (d, 3H, CH$_3$CH), 1.58 (d, 2H, CH$_2$N), 2.01 (t, 2H, CH$_2$N), 2.10 (t, 2H, CH$_2$C), 2.28 (s, 3H, NCH$_3$), 2.53 (s, 2H, CH$_2$CO), 2.82 (d, 2H, CH$_2$C), 2.94 (s, 3H, CH$_3$SO$_2$O), 3.44 (dd, 1H, NCH$_2$CH), 3.79 (q, 1H, NCH$_2$CH), 5.04 (m, 1H, CHOMs). Elemental Analysis: (C$_{13}$H$_{22}$N$_2$O$_5$S) Cal: C, 49.04; H, 6.96; N, 8.80; S, 10.07. Found: C, 48.84; H, 6.75; N, 8.51; S, 10.37.

[I] Synthesis of 2-(2-fluoroethyl)-8-methyl-2,8-diazaspiro[4,5]decane-1,3-dione (9; FIG. 3). A solution of compound 4 (0.3 g, 1.65 mmol) dissolved in fresh distilled DMF (2 mL) was treated with 95% NaH (0.05 g, 1.90 mmol) in mineral oil and the mixture was stirred for 1.5 h at 50° C. and then there was added a solution of 1-bromo-2-fluoroethane (0.33 g, 2.6 mmol) in DMF (2 mL) over the period of 50 min and the mixture was stirred for 4 h at 75 to 80° C. Then the mixture was filtered with active charcoal carbon (0.01 g) and the filtrate was evaporated in vacuo. The residue was extracted with chloroform (3×50 mL) and the precipitated salts were filtered off, the filtrate was filtered through a layer of neutral Al$_2$O$_3$ (activity II). The solvent was evaporated under the reduced pressure to give a colorless solid. The pure product was obtained as a colorless powder by flash chromatography with 15% methanol in CH$_2$Cl$_2$ (175 mg; yield 46%). $^1$H NMR (CDCl$_3$-d) δ 1.48 (d, 2H, CH$_2$N), 1.96 (t, 2H, CH$_2$C), 2.08 (t, 2H, CH$_2$N), 2.24 (s, 3H, NCH$_3$), 2.52 (s, 2H, CH$_2$CO), 2.81 (d, 2H, CH$_2$C), 3.75 (tt, 2H, NCH$_2$), 4.48 (tt, 2H, CH$_2$F). Elemental Analysis: (C$_{11}$H$_{17}$FN$_2$O$_2$) Cal: C, 57.88; H, 7.51; N, 12.27; F, 8.32. Found: C, 57.61; H, 7.79; N, 12.13; F, 7.73.

Note: In the preparation of compound 9, the method of using compound 6 reacted with TBAF (tetrabutylammonium fluoride in THF) in order to replace the Ms-group with a fluoro-group was unsuccessful due to excess TBAF which could not be separated from the product 9, both have an overlap R$_f$ values in TLC and flash chromatography in elution systems such as 10-20% methanol in CH$_2$Cl$_2$. See *Nucl. Med. Biol.* 1993, 20(1), 81.

[J] Synthesis of 2-(2-fluoropropyl)-8-methyl-2,8-diazaspiro[4,5]decane-1,3-dione (10; FIG. 3). To a solution of compound 4 (1.2 g, 6.5 mmol) in DMF (10 mL) was slowly added 95% NaH in mineral oil (0.2 g, 7.8 mmol). The mixture was stirred at 65° C. for 1 h. To the mixture, a solution of 1-bromo-2-fluoropropane (1.1 g, 7.8 mmol) in DMF (6 mL) was added over 80 min until the brown bubbles all dissolved and the mixture became a clear yellow solution, then the temperature of the oil bath was raised up to 70° C. and kept overnight. After cooling to room temperature, the mixture was added charcoal carbon (0.1 g) and filtered through a layer of Celite. The filtrate was evaporated to dryness under the reduced pressure and the residue was extracted with chloroform (3×60 mL). The collected chloroform was filtered off the insoluble materials and then filtered through a layer of neutral Al$_2$O$_3$ (activity II). The filtrate was evaporated in the reduced pressure to give a yellow solid. The crude product was purified by crystallization in hexanes to provide a colorless powder (1.2 g; yield 76%). $^1$H NMR (CDCl$_3$-d) δ 1.33 (q, 3H, CH$_3$CH), 1.49 (d, 2H, CH$_2$N), 1.99 (t, 2H, CH$_2$N), 2.13 (t, 2H, CH$_2$C), 2.28 (s, 3H, NCH$_3$), 2.57 (s, 2H, CH$_2$CO), 2.83 (d, 2H, CH$_2$C), 3.48 (d-q, 1H, NCH$_2$CHF), 3.78 (d-t, 1H, NCH$_2$CHF), 4.84 (d-m, 1H, CHF). Elemental Analysis: (C$_{12}$H$_{19}$FN$_2$O$_2$) Cal: 59.49; H, 7.90; N, 11.56; F, 7.84. Found: C, 59.49; H, 8.06; N, 11.55; F, 7.69.

Note: In the preparation of compound 10, the method of using compound 7 directly reacted with DAST (diethylaminosulfur trifluoride) in CH$_2$Cl$_2$ has been proved to provide the product 10 only with poor yield 10-20%. See *J. Org. Chem.* 1975, 40(5), 574.

[K] Synthesis of 1-bromo-2-fluoroethane. See *J. Org. Chem.* 1975, 40(5), 574. 1-Bromoethanol (1.65 g, 12.5 mmol) was added dropwise to a solution of dimethylaminosulfur trifluoride (DAST) (2.0 g, 12.5 mmol) in diglyme (8 mL) cooled to −50° C. in a bath of dry-ice and acetone. The reaction mixture was warmed to room temperature, and continued to stirring at room temperature for 1 h. The most volatile portion was distilled at 68-75° C. for collection in dry-ice traps by a hood vacuum. The distillate was washed with water (4 mL), 5% sodium bicarbonate solution, dried over MgSO$_4$, and redistilled to give product as a colorless oil (1.4 g; yield 88%). $^1$H NMR (CDCl$_3$-d) δ 3.50 (t-t, 2H, CH$_2$Br), 4.62 (t-t, 2H, CH$_2$F).

[L] Synthesis of 1-bromo-2-fluoropropane. This compound was synthesized as reported in the literature; see *Organic Syntheses* 2004, 10, 128; and *Organic Syntheses* 1999, 76, 159. $^1$H NMR (CDCl$_3$-d) δ 1.41 (d-d, 3H, CH$_3$CH), 3.44 (d-d, 2H, CH$_2$Br), 4.80 (m-m, 1H, CHF).

Example 2

Figure 4:
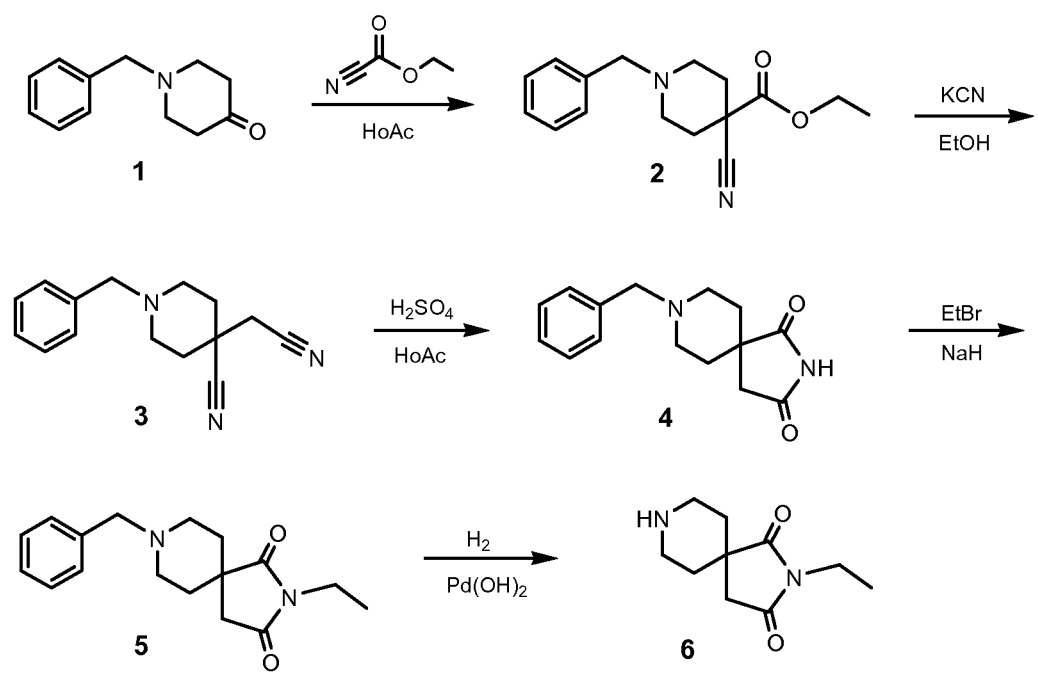
FIG. 4 depicts one approach to the synthesis of N-2-ethyl-2,8-diazaspiro[4,5]decane-1,3-dione.

FIG. 4 depicts one approach to the synthesis of N-2-ethyl-2,8-diazaspiro[4,5]decane-1,3-dione (6; FIG. 4). The preparation of 2-ethyl-2,8-diazaspiro[4,5]decane-1,3-dione 6 was done according to a modified version of a known procedure. See Irie, O., Iwasaki, G. et al., WO 2004/076455; which is hereby incorporated by reference in its entirety. Synthetic protocols for the synthesis of the compounds depicted in FIG. 4 are presented below.

[A] Synthesis of 1-benzyl-piperidin-4-ylidene)-cyanoacetate (2; FIG. 4). A solution of 1-benzyl-piperidin-4-one (75.1 g, 0.40 mol) in toluene (9400 mL), ethyl cyanoacetate (50.6 mL, 0.48 mol) and acetic acid (918.2 mL, 0.32 mol) was refluxed for 4 hr. The mixture was quenched with ice-water and extracted with diethyl ether. The combined extracts were washed with water, brine and dried over Na$_2$SO$_4$ to give ethyl(1-benzyl-piperidin-4-ylidene)cyanoacetate in quantitative yield. R$_f$=0.53 (hexane:AcOEt=1:1).

[B] Synthesis of 1-benzyl-4-cyanomethylpiperidine-4-carbonitrile (3; FIG. 4). A solution of (1-benzyl-piperidin-4-ylidene)cyanoacetate (112.9 g, 0.40 mol) in ethanol (500 mL) and water (100 mL), potassium cyanide (64.6 g, 0.99 mol) heated at 65° C. for 24 h. After removal of ethanol, water was added to the residue. The water phase was extracted with ether and the combined ether extract was washed with water, brine and dried over Na2SO4 to give 77.7 g of 1-benzyl-4-cyanomethylpiperidine-4-carbonitrile. Rf=0.38 (hexane:AcOEt=1:1).

[C] Synthesis of 8-benzyl-2,8-diazaspiro[4,5]decane-1,3-dione (4; FIG. 4). 1-Benzyl-4-cyanomethylpiperidine-4-carbonitrile (27.2 g, 0.114 mol), acetic acid (56.8 mL) and sulfuric acid (11.8 mL) were heated at 125° C. for 1 hr. The mixture was cooled to 25° C. and sat. NaOH was used to adjust the pH to 6. The mixture was extracted with dichloromethane. The combined extracts were washed with water, brine, dried over Na$_2$SO$_4$ and evaporated to give 8-benzyl-2,8-diazaspiro[4,5]decane-1,3-dione. R$_f$=0.40 (CH$_2$Cl$_2$:MeOH=10:1).

[D] Synthesis of 8-benzyl-N-2-ethyl-2,8-diazaspiro[4,5]decane-1,3-dione (5; FIG. 4). 8-Benzyl-2,8-diazaspiro[4,5]decane-1,3-dione in DMF was treated with NaH (1.2 eq) and 2-bromoethane was added. The mixture was heated at 100° C. for 2 hr. The mixture was cooled to 25° C. and poured over ice-water and extracted with dichloromethane. The combined dichloromethane extract was washed with water, brine, dried over Na$_2$SO$_4$ and evaporated to give 8-benzyl-N-2-ethyl-2,8-diazaspiro[4,5]decane-1,3-dione.

[E] Synthesis of N-2-ethyl-2,8-diazaspiro[4,5]decane-1,3-dione (6; FIG. 4). 8-Benzyl-N-2-ethyl-2,8-diazaspiro[4,5]decane-1,3-dione (2.8 g) and Pd(OH)$_2$ (0.8 g) in ethanol (50 mL) and acetic acid (0.5 mL) was stirred under H$_2$ at 25° C. for 15 hr. The catalyst was removed by filtration and ethanol was evaporated to give N-2-ethyl-2,8-diazaspiro[4,5]decane-1,3-dione.

Example 3

Figure 6:
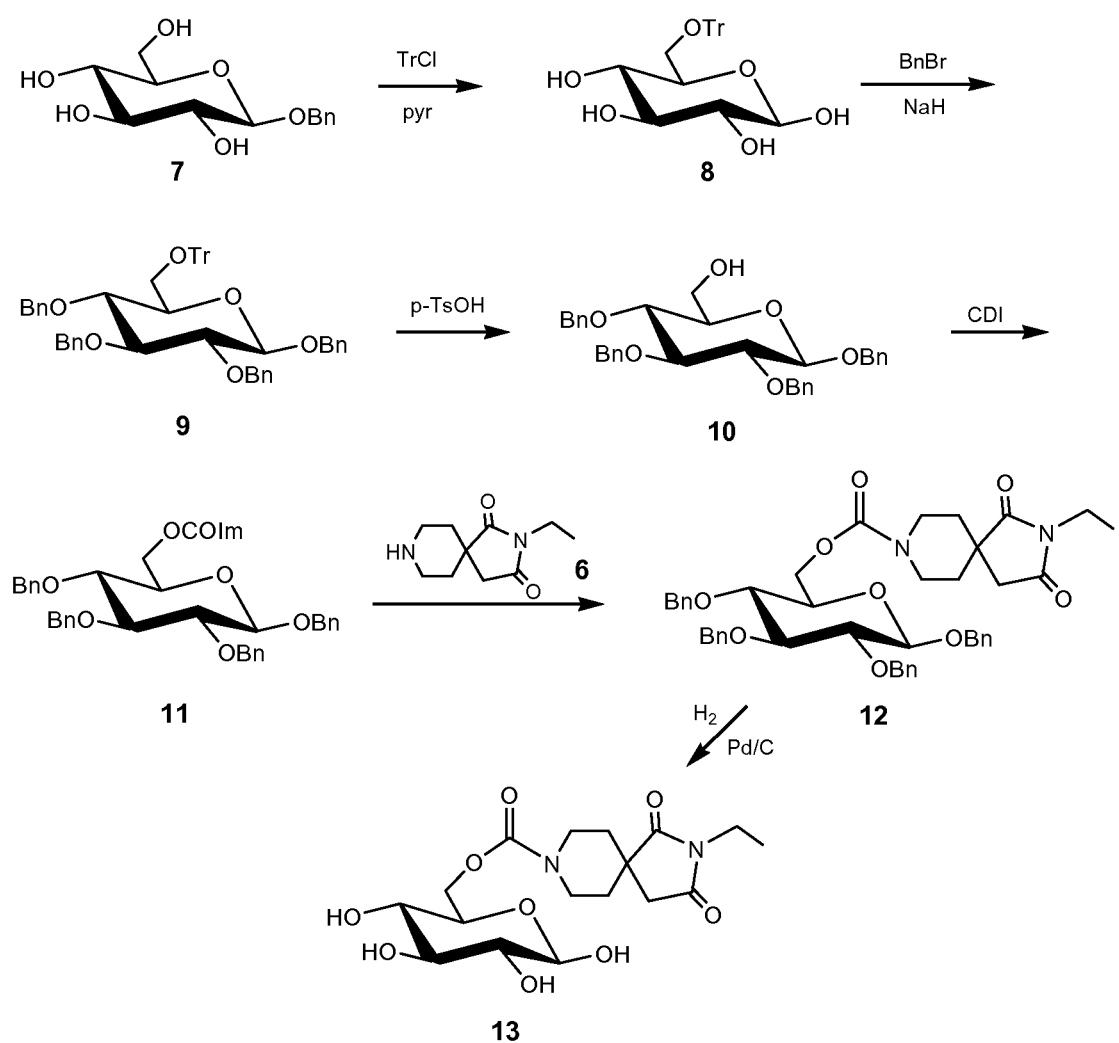
FIG. 6 depicts one approach to the synthesis of 6-O—[N—(N-2-ethyl-2,8-diazaspiro[4,5]decane-1,3-dione)aminocarbonyl]-α,β-D-glucopyranose.

One approach to the synthesis of 6-O—[N—(N-2-ethyl-2,8-diazaspiro[4,5]decane-1,3-dione)aminocarbonyl]-α,β-D-glucopyranose (13; FIG. 6) is depicted in FIG. 6. 1-O-Benzyl-β-D-Glucoside 7 is commercially available or it can be made in one step from almond β-D-glucosidase-catalyzed glycosidation of β-D-glucose and benzyl alcohol. See *Carbohydrate Res.* 1995, 279, 315. In addition, benzyl 2,3,4-tri-O-benzyl-6-O-imidazolylcarbonyl-β-D-glucopyranoside (11; FIG. 6) can be prepared via a known procedure. See *Org. Biomol. Chem.* 2003, 1, 767-771. Synthetic protocols for the synthesis of the compounds depicted in FIG. 6 are presented below.

[A] Synthesis of benzyl 6-O-trityl-β-D-glucopyranside (8; FIG. 6). A solution of 1 (1.71 g, 6.33 mmol) in pyridine (14 mL) is treated with trityl chloride (2.65 g, 9.5 mmol) and DMAP (155 mg, 1.27 mmol) at 60° C. for 7 hr. The reaction mixture is cooled at room temperature, MeOH (4 mL) added, and the solvents were evaporated. The residue is purified by flash chromatography (hexane-AcOEt, 5:1 to give benzyl 6-O-trityl-β-D-glucopyranside as a solid. Rf=0.22 (hexane-AcOEt, 1:2); m.p. 72-74° C.; [α]D$^{20}$−52.0° (c 1, CHCl$_3$).

[B] Synthesis of benzyl 2,3,4-tri-O-benzyl-6-O-trityl-β-D-glucopyranoside (9; FIG. 6). A solution of benzyl 6-O-trityl-β-D-glucopyranside (3.58 g, 6.99 mmol) in dry DMF (23 mL) is treated with 95% NaH (630 mg, 26.2 mmol) at 0° C. After 10 min, benzyl bromide (2.74 mL, 23.1 mmol) is added and the reaction is allowed to proceed at room temperature overnight. The reaction mixture is quenched with methanol and concentrated. The residue is dissolved in ether (50 mL), washed with water (4×30 mL), dried (Na$_2$SO$_4$), and concentrated. The residue is purified by flash chromatography (hexane-AcOEt, 20:1; 10:1) to give benzyl 2,3,4-tri-O-benzyl-6-O-trityl-β-D-glucopyranoside as a syrup. Rf=0.29 (hexane-AcOEt, 10:1).

[C] Synthesis of benzyl 2,3,4-tri-O-benzyl-β-D-glucopyranoside (10; FIG. 6). A solution of benzyl 2,3,4-tri-O-benzyl-6-O-trityl-β-D-glucopyranoside (4.41 g, 5.64 mmol) in CH$_2$Cl$_2$-MeOH (1:2, 56.4 mL) is treated with pTsOH (0.21 g, 1.13 mmol) at room temperature for 6 hr. After this time, triethylamine (0.16 mL, 1.13 mmol) is added, the mixture concentrated and the residue dissolved in ether (60 mL). The organic solution is washed with water (2×30 mL), brine (30 mL), dried (Na$_2$SO$_4$), and concentrated. The residue is fractionated by flash chromatography (hexane-AcOEt, 8:1; 5:1; 3:1) to give benzyl 2,3,4-tri-O-benzyl-β-D-glucopyranoside as a solid. R$_f$=0.21 (hexane-AcOEt, 3:1); m.p. 99-101° C.; [α]D$^{20}$−10.4° (c 1, CHCl$_3$).

[D] Synthesis of benzyl 2,3,4-tri-O-benzyl-6-O-imidazolylcarbonyl-β-D-glucopyranoside (11; FIG. 6). A solution of benzyl 2,3,4-tri-O-benzyl-β-D-glucopyranoside (2.53 g, 4.69 mmol) in dioxane (5.3 mL) and N,N-carbonyldiimidazol (0.91 g, 5.63 mmol) is stirred at room temperature for 1 hr. After this time, the mixture is concentrated and the residue purified by flash chromatography (hexane-AcOEt 3:1) to give benzyl 2,3,4-tri-O-benzyl-6-O-imidazolylcarbonyl-β-D-glucopyranoside as a solid. R$_f$=0.22 (hexane-AcOEt, 2:1); m.p. 105-108° C.; [α]D$^{20}$+28.9° (c 1, CHCl$_3$).

[E] Synthesis of benzyl 2,3,4-tri-O-benzyl-6-O—[N-2-ethyl-2,8-diazaspiro[4,5]decane-1,3-dione) aminocarbonyl]-β-D-glucopyranoside (12; FIG. 6). A mixture of benzyl 2,3,4-tri-O-benzyl-6-O-imidazolylcarbonyl-β-D-glucopyranoside (2.78 g, 4.39 mmol), N-2-ethyl-2,8-diazaspiro[4,5]decane-1,3-dione (1.63 g, 3.65 mmol), triethylamine (5 mL) and THF (15 mL) is stirred at 80° C. for 8 hr. After this time, the solvents were removed and the residue was purified by flash chromatography to give benzyl 2,3,4-tri-O-benzyl-6-O—[N-2-ethyl-2,8-diazaspiro[4,5]decane-1,3-dione) aminocarbonyl]-β-D-glucopyranoside.

[F] Synthesis of 6-O—[N-2-ethyl-2,8-diazaspiro[4,5]decane-1,3-dione)aminocarbonyl]-α,β-D-glucopyranose (13; FIG. 6). A solution of the glycoconjugate (0.01M) in AcOEt-MeOH-toluene (4:3:3) was hydrogenolyzed over 10% Pd/C (1.1 g per mmol) for 1-5 hr, when TLC (AcOEt-AcOH-MeOH, 4:1:1) shows the complete conversion product. The reaction mixture is filtered through Celite, and concentrated. The residue is dissolved in methanol/water (95:5) and freeze-dried, to give 6-O—[N-2-ethyl-2,8-diazaspiro[4,5]decane-1,3-dione)aminocarbonyl]-α,β-D-glucopyranose.

Example 4

Figure 7:
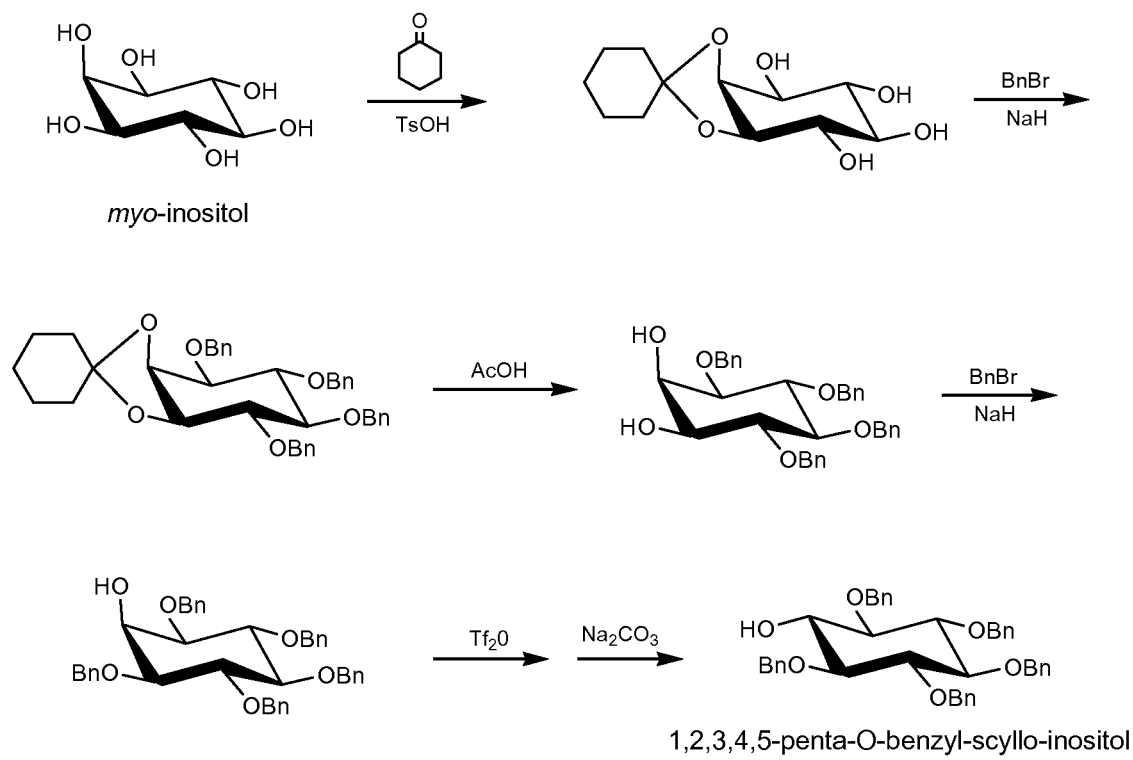
FIG. 7 depicts one approach to the synthesis of 1,2,3,4,5-penta-O-benzyl-scyllo-inositol.

One approach to the synthesis of 1,2,3,4,5-penta-O-benzyl-scyllo-inositol is shown in FIG. 7. Preparation of 1,2-O-Cyclohexylidene myo-inositol was done using a modified version of the method described by Angyal. See *J. Chem. Soc.* 1961, 4116. 1,2,3,4,5,-Penta-O-benzylmyo-inositol was synthesized according to a known procedure of Lowe. See *J. Chem. Soc. Perkin Trans* 1. 1991, 1249. Synthetic protocols for the synthesis of the compounds depicted in FIG. 7 are presented below.

[A] Synthesis of 1,2-β-cyclohexylidene myo-inositol (2; FIG. 7). Myo-inositol (5 g, 28 mmol) cyclohexanone (50 mL), p-toluene sulfonic acid (36 mg), DMF (5 mL), and benzene (25 mL) were refluxed in a Dean-Stark apparatus for 16 hr. The clear solution was cooled to 40° C. and benzene (25 mL), petroleum ether (25 mL), and ethanol (12 mL) were added. To this solution was added p-toluene sulfonic acid (0.3 g) and the mixture was stirred at 4° C. for 2 hr. Triethylamine (0.3 mL) was added and the mixture was allowed to stand at −20° C. for 16 hr. The suspension was filtered and the filtrate was heated in ethanol (100 mL) and triethylamine (0.5 mL) at 80° C. for 1 hr. After cooling, crystalline (±)-cis-1,2-O-cyclohexylidene myo-inositol was collected by filtration and dried (5.3 g, 74%), m.p. 175-180° C. (Lit 178° C.).

[B] Synthesis of 1,4,5,6-tetra-O-benzyl-2,3-O-cyclohexylidene myo-inositol. 1,2-O-cyclohexylidene myo-inositol is treated with benzyl bromide and sodium hydride in DMF heated for 16 hr. The solution is poured over ice-water and extracted with ether. The combined extracts are washed with water, brine and dried. The solvent is evaporated in vacuo and the residue is chromatographed on silica gel to give 1,4,5,6-tetra-O-benzyl-2,3-O-cyclohexylidene myo-inositol; mp 113-115° C.

[C] Synthesis of 1,4,5,6-Tetra-O-benzylmyo-inositol. 1,4,5,6-tetra-O-benzyl-2,3-O-cyclohexylidene myo-inositol is heated for 4 hr at 100° C. with glacial acetic acid (20 mL) and water (5 mL). The solution is evaporated in vacuo and the residue is chromatographed on silica gel to give 1,4,5,6-tetra-O-benzylmyo-inositol.

[D] Synthesis of 1,3,4,5,6-Penta-O-benzylmyo-inositol. A solution of 1,4,5,6-tetra-O-benzyllmyo-inositol in benzene is treated with benzyl bromide and sodium hydride. The mixture was stirred at 100° C. for 2 hr. The reaction mixture is poured over ice-water and extracted with ether. The organic layer was separated and washed successively with saturated aqueous NaHCO$_3$ and brine. The solution was evaporated in vacuo and the residue was chromatographed on silica gel to give 1,3,4,5,6-penta-O-benzylmyo-inositol.

[E] Synthesis of 1,2,3,4,5-penta-O-benzyl-scyllo-inositol. 1,3,4,5,6-penta-O-benzylmyo-inositol in anhydrous and methylene chloride (20 mL) and dry pyridine is treated with trifluoromethylsulfonyl anhydride at −60° C. The reaction mixture is allowed to warm to 25° C. and kept for 2 hr. The solution is quenched with water, diluted with methylene chloride and washed with saturated aqueous NaHCO$_3$. Solvent is evaporated in vacuo and the residue is chromatographed on silica gel to give 1,2,3,4,5-penta-O-benzyl-scyllo-inositol.

Example 5

Figure 8:
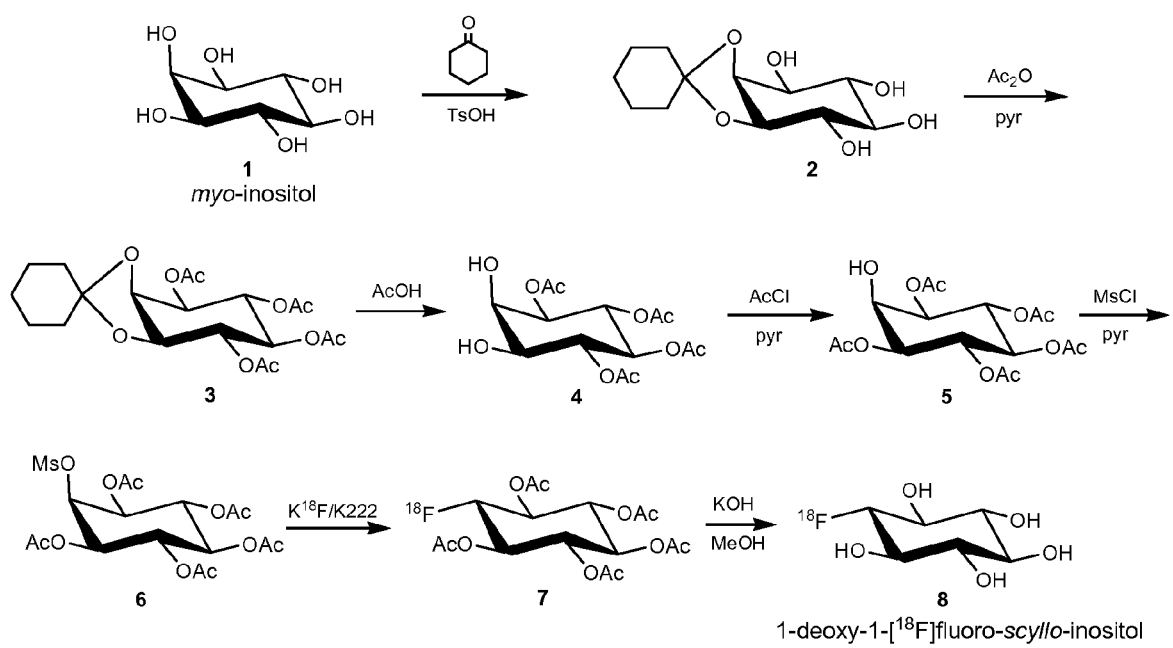
FIG. 8 depicts one approach to the synthesis of 1-deoxy-1-F-18-fluoro-scyllo-inositol

One approach to the synthesis of 1-deoxy-1-[18F]fluoro-scyllo-inositol is presented in FIG. 8. Preparation of 1,4,5,6-tetra-O-acetyl-myo-inositol (4; FIG. 8) was done using a modified version of the method described by Angyal. See *J. Chem. Soc.* 1961, 4116. 1,3,4,5,6-Penta-O-acetylmyo-inositol (5; FIG. 8) was synthesized according to a known procedure of Hosoda. See *Bioorg. Med. Chem.* 2002, 10, 1855. Synthetic protocols for the synthesis of the compounds depicted in FIG. 8 are presented below.

[A] Synthesis of 1,2-O-cyclohexylidene myo-inositol (2; FIG. 8). Myo-inositol (5 g, 28 mmol) cyclohexanone (50 mL), p-toluene sulfonic acid (36 mg), DMF (5 mL), and benzene (25 mL) were refluxed in a Dean-Stark apparatus for 16 hr. The clear solution was cooled to 40° C. and benzene (25 mL), petroleum ether (25 mL), and ethanol (12 mL) were added. To this solution was added p-toluene sulfonic acid (0.3 g) and the mixture was stirred at 4° C. for 2 hr. Triethylamine (0.3 mL) was added and the mixture was allowed to stand at −20° C. for 16 hr. The suspension was filtered and the filtrate was heated in ethanol (100 mL) and triethylamine (0.5 mL) at 80° C. for 1 hr. After cooling, crystalline (±)-cis-1,2-O-cyclohexylidene myo-inositol was collected by filtration and dried (5.3 g, 74%), m.p. 175-180° C. (Lit 178° C.).

[B] Synthesis of 1,4,5,6-tetra-O-acetyl-2,3-O-cyclohexylidene myo-inositol (3; FIG. 8). 1,2-O-cyclohexylidene myo-inositol (4.8 g, 17.4 mmol) was heated at 90° C. for 2 hr with anhydrous pyridine (30 mL) and acetic anhydride (32 mL). The solution was evaporated in vacuo and the residue was chromatographed on silica gel using 96:4 methylene chloride/methanol to give 1,4,5,6-tetra-O-acetyl-2,3-O-cyclohexylidene myo-inositol (6.8 g, 85%), mp 112-114° C. (lit 118° C.).

[C] Synthesis of 1,4,5,6-tetra-O-acetylmyo-inositol (4; FIG. 8). 1,4,5,6-tetra-β-acetyl-2,3-β-cyclohexylidene myo-inositol (5 g, 11.7 mmol) was heated for 4 hr at 100° C. with glacial acetic acid (20 mL) and water (5 mL). The solution was evaporated in vacuo and the residue was chromatographed on silica gel to give 1,3,4,5,6-penta-O-acetylmyo-inositol as a monohydrate.

[D] Synthesis of 1,3,4,5,6-penta-O-acetylmyo-inositol (5; FIG. 8). To a solution of 1,3,4,5,6-penta-O-acetylmyo-inositol (2 g, 5.7 mmol) in anhydrous pyridine (5 mL) and methylene chloride (20 mL) was added successively 4-(dimethylamino)pyridine (2 mg) and acetyl chloride (0.9 g, 11.5 mmol). The mixture was stirred at 25° C. for 16 hr. Water was added to the reaction mixture and the organic layer was separated and washed successively with saturated aqueous $NaHCO_3$ and brine. The solution was evaporated in vacuo and the residue was chromatographed on silica gel to give 1,3,4,5,6-penta-O-acetylmyo-inositol.

[E] Synthesis of 1,3,4,5,6-penta-O-acetyl-2-O-methanesulfonyl myo-inositol (6; FIG. 8). 1,3,4,5,6-penta-O-acetylmyo-inositol (1 g, 2.6 mmol) in anhydrous pyridine (5 mL) and methylene chloride (20 mL) was treated with 4-(dimethylamino)pyridine (2 mg) and methanesulfonyl chloride (0.6 g, 5.2 mmol) at 25° C. for 16 hr. The solution was evaporated in vacuo and the residue was chromatographed on silica gel to give 1,3,4,5,6-penta-O-acetyl-2-O-methanesulfonyl myo-inositol.

[F] Synthesis of 1-deoxy-1-[18F]fluoro-scyllo-inositol (8; FIG. 8). A Wheaton 5-mL reaction vial containing fluorine-18 (100 mCi) in 1 mL of $^{18}O$-enriched water, Kryptofix 2.2.2. (8 mg), and potassium carbonate (2 mg) was heated at 120° C. and water was evaporated with the aid of a nitrogen gas flow. The $K^{18}F$/Kryptofix complex was dried three successive times by the addition of 1 mL acetonitrile followed by evaporation of the solvent using a nitrogen flow. A solution of 2 mg of mesylate 6 in 0.1 mL acetonitrile was added to the sealed vial and fluorination was performed at 140° C. for 10 min. After cooling to room temperature, the reaction mixture was passed through a silica gel Sep-Pak using methylene chloride (3 mL) and the solvent removed using a nitrogen flow. A mixture of 0.5 mL 1 M lithium hydroxide and 1 mL methanol was added to the reaction vial and the vial heated at 80° C. for 20 min. Solvent was removed, and 1-deoxy-1-[$^{18}F$]fluoro-scyllo-inositol was purified on a C18 Sep-Pak using saline and filtered (MillexGV 0.22 µm).

Example 6

Figure 9:
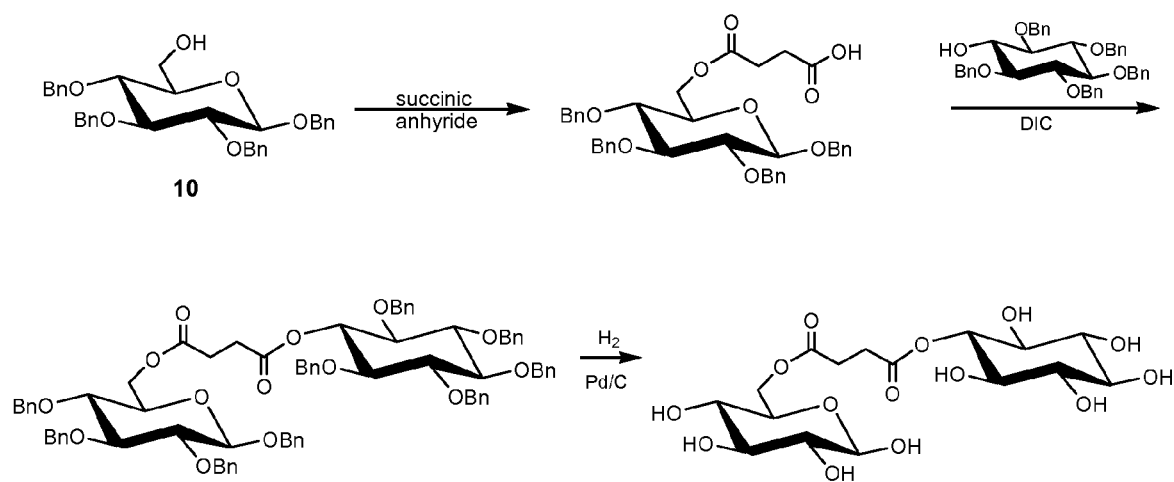
FIG. 9 depicts one approach to the synthesis of 6-O-[(β-D-glucopyranose-6-yl)-succinyl]-scyllo-inositol.

One approach to the synthesis of 6-O-[(β-D-glucopyranose 6-yl)-succinyl]-scyllo-inositol is shown in FIG. 9. Benzyl 2,3,4-tri-O-benzyl-β-D-glucopyranoside 6-(hydrogen succinate) is prepared from a known procedure. See *Org. Biomol. Chem.* 2003, 1, 767-771. Synthetic protocols for the synthesis of the compounds depicted in FIG. 9 are presented below.

[A] Synthesis of benzyl 2,3,4-tri-O-benzyl-β-D-glucopyranoside 6-(hydrogen succinate). A solution of benzyl 2,3,4-tri-O-benzyl-β-D-glucopyranoside (10; FIG. 9) in pyridine is treated with succinic anhydride and DMAP and stirred at room temperature for 16 h. The mixture is concentrated and the residue dissolved in $CH_2Cl_2$ and washed successively with 5% aqueous HCl (3×15 mL), sat. aqueous $NaHCO_3$ (3×15 mL), and water (3×15 mL). The organic solution is dried ($Na_2SO_4$), and concentrated to give benzyl 2,3,4-tri-O-benzyl-β-D-glucopyranoside 6-(hydrogen succinate) as a solid. $R_f$=0.56 (hexane-AcOEt, 2:1); m.p. 75-80° C.; [α]$D^{20}$−7.7° (c 1, $CHCl_3$).

[B] Synthesis of benzyl-[(benzyl 2,3,4-tri-O-benzyl-β-D-glucopyranoside 6-yl)-succinyl]-scyllo-inositol. A solution of benzyl 2,3,4-tri-O-benzyl-β-D-glucopyranoside 6-(hydrogen succinate) in $CH_2Cl_2$ (2.5 mL) is added dropwise to a solution of 1,2,3,4,5,-penta-O-benzyl-scyllo-inositol and N,N'-diisopropylcarbodiimide in $CH_2Cl_2$ (10 ml) at 0° C. The mixture is allowed to stir 24 h at room temperature, then, diluted with $CH_2Cl_2$ (15 mL), washed with 1N $KHSO_4$ (2×10 mL), sat. aqueous $NaHCO_3$ (2×10 mL), water (2×10 mL), and sat. NaCl (10 mL). The organic solution is dried ($Na_2SO_4$), the solvent removed under reduced pressure, and the residue purified by flash chromatography to give benzyl-[(benzyl 2,3,4-tri-O-benzyl-β-D-glucopyranoside 6-yl)-succinyl]-scyllo-inositol.

[C] Synthesis of 6-O-[(β-D-glucopyranose 6-yl)-succinyl]-scyllo-inositol. Benzyl-[(benzyl 2,3,4-tri-O-benzyl-β-D-glucopyranoside 6-yl)-succinyl]-scyllo-inositol in 1:1 AcOEt-MeOH is treated with TFA and Pd/C and stirring under hydrogen for 12 h. The reaction mixture is filtered and concentrated, and the residue is dissolved in $CH_3NO_2$-water (95:5) and freeze-dried, to give 6-O-[(β-D-glucopyranose 6-yl)-succinyl]-scyllo-inositol.

Example 7

RS-86 (2-ethyl-8-methyl-2,8-diazaspiro[4,5]decane-1,3-dione), a M1 muscarinic receptor agonist, was radiofluorinated and brain accumulation evaluated and compared to that of its C-11 labeled analog. Alzheimer's disease (AD) is associated with reductions in the presynaptic marker choline acetyltransferase activity and M2 muscarine receptors which precedes other pathologic changes. A number of M1 agonists have been developed to treat AD that increase acetylcholine transmission in the brain alleviating memory loss. M1 postsynaptic receptors are thought to be upregulated. Therefore, a M1 specific radioligand may show higher than normal accumulation in patients, and hence, serve as a potential early diagnostic method for AD.

As described above, 2-(2-methanesulfonylethyl)-8-methyl-2,8-diazaspiro[4,5]decane-1,3-dione was prepared in five steps. The RS-86 mesylate (2 mg) in acetonitrile (0.1 mL) was added to a sealed vial containing dried $K^{18}F$/kryptofix and heated at 120° C. for 10 min. The mixture was diluted with water (0.2 mL) and purified by HPLC (C-18 column 250×10 mm, flow 6 mL/min, PBS/acetonitrile (95:5). The fraction containing [$^{18}F$]fluoro-RS 86 was evaporated to dryness and the activity dissolved in PBS before filtering. Biodistribution was performed in rats at 5, 30 and 60 min.

[$^{18}F$]fluoro-RS 86 was prepared in 20% yield (EOS) with 95% chemical and 98% radio purity. Brain uptake at 5, 30 and 60 min was 0.27, 0.54, 0.48, respectively. Blood, liver and stomach were 0.3%, 0.64% and 0.90% with the greatest uptake in the kidneys (2.5%) at 30 min. Defluorination was minimal (0.42% in bone at 30 min).

The lower brain uptake of [$^{18}F$]fluoro-RS 86 compared to [$^{11}C$]RS-86 (0.54% vs. 1%) may be due to the location of the fluoride label on the ligand. These preliminary results suggest that [$^{18}F$]fluoro-RS 86 accumulates in rat brain, however further studies are needed to determine whether the distribution in the brain reflects M1 mAChR concentration.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A compound, or a pharmaceutically acceptable salt thereof, represented by formula I:

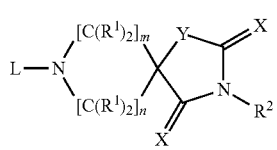

wherein, independently for each occurrence,
X is —O—;
Y is —C($R^1$)$_2$—;
L is —$R^3$, —C(=O)$R^3$, —C(=O)[C($R^1$)$_2$]$_p$$R^3$, or —[C($R^1$)$_2$]$_p$C(=O)$R^3$;
$R^1$ is hydrogen, halo, alkyl, haloalkyl, perhaloalkyl, fluoroalkyl, perfluoroalkyl, hydroxy, or alkoxy;
$R^2$ is an unsubstituted alkyl, or alkyl substituted with one or more substituents selected from the group consisting of halo, hydroxy, alkoxy, and amino;
$R^3$ is

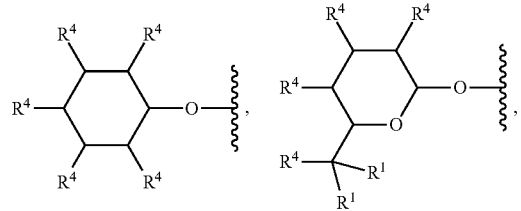

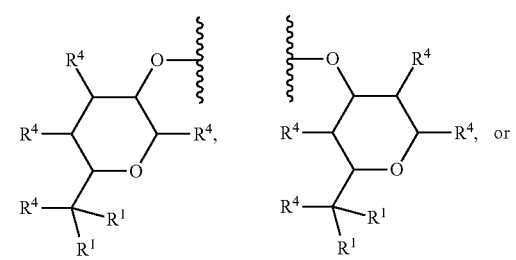

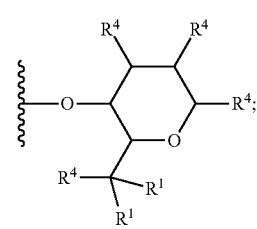

$R^4$ is hydrogen, halo, alkyl, haloalkyl, perhaloalkyl, fluoroalkyl, perfluoroalkyl, hydroxy, or alkoxy;
m is 1, 2 or 3;
n is 1, 2 or 3;
m plus n is 3 or 4; and
p is 1-10 inclusive.

2. The compound of claim 1, wherein $R^1$ or $R^4$ is halo, or $R^1$, $R^2$, or $R^4$ comprises at least one halo substituent; and the halo or the halo substituent is selected from the group consisting of $^{18}$F, $^{76}$Br, $^{77}$Br, $^{123}$I, $^{124}$I and $^{125}$I.

3. The compound of claim 1, wherein $R^2$ is unsubstituted alkyl, or alkyl substituted with —F, —Cl, —Br or —I.

4. The compound of claim 1, wherein $R^3$ is

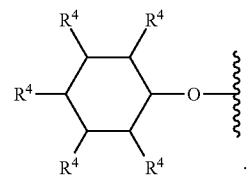

5. The compound of claim 1, wherein $R^3$ is

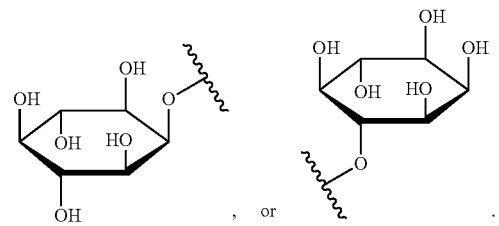

6. The compound of claim 1, wherein $R^3$ is

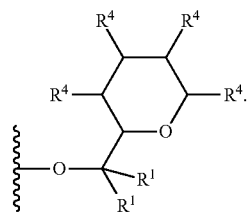

7. The compound of claim 1, wherein L is —C(=O)$R^3$; and one instance of $R^4$ is —$^{18}$F.

8. The compound of claim 1, wherein L is —C(=O)$R^3$; $R^3$ is

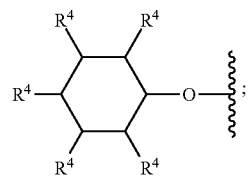

and $R^2$ is unsubstituted alkyl.

9. The compound of claim 1, wherein L is —C(=O)R³; R³ is

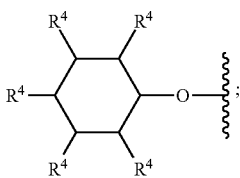

and R² is ethyl.

10. The compound of claim 1, wherein the compound is represented by

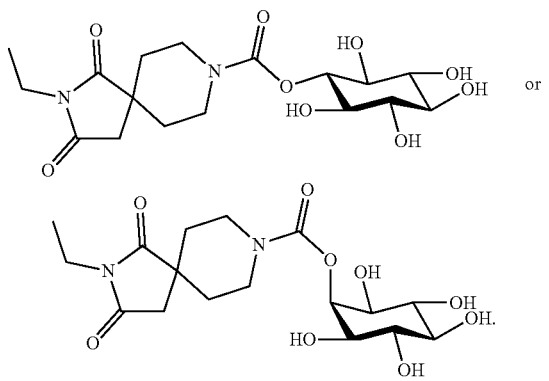

11. A compound, or a pharmaceutically acceptable salt thereof, represented by formula I:

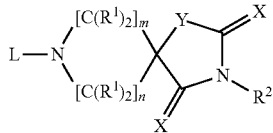

wherein, independently for each occurrence,

X is —O—;
Y is —C(R¹)₂—;
L is —R³;
R¹ is hydrogen, halo, alkyl, haloalkyl, perhaloalkyl, fluoroalkyl, perfluoroalkyl, hydroxy, or alkoxy;
R² is alkyl substituted with one or more —F;
R³ is alkyl or heteroalkyl;
m is 1, 2 or 3;
n is 1, 2 or 3;
m plus n is 3 or 4; and
p is 1-10 inclusive.

12. The compound of claim 11, wherein
(a) R¹ is halo, or R¹ or R³ comprises at least one halo substituent; and the halo or the halo substituent is selected from the group consisting of $^{18}$F, $^{76}$Br, $^{77}$Br, $^{123}$I, $^{124}$I and $^{125}$I; or
(b) R² is alkyl substituted with —$^{18}$F.

13. The compound of claim 11, wherein R² is alkyl substituted with —$^{18}$F.

14. The compound of claim 11, wherein R² is alkyl substituted with —$^{18}$F; and R³ is alkyl.

15. The compound of claim 11, wherein the compound is represented by

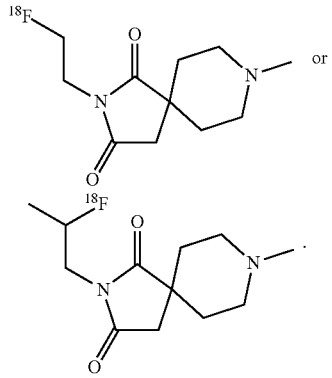

* * * * *